US012109297B2

(12) United States Patent
Taupin et al.

(10) Patent No.: US 12,109,297 B2
(45) Date of Patent: Oct. 8, 2024

(54) PROCESS FOR TREATING KERATIN FIBERS EMPLOYING AN ANHYDRIDE ACRYLIC POLYMER IN OILY DISPERSION AND AN AMINE COMPOUND

(71) Applicant: L'OREAL, Paris (FR)

(72) Inventors: Simon Taupin, Aulnay-sous-Bois (FR); Julien Portal, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/284,377

(22) PCT Filed: Oct. 11, 2019

(86) PCT No.: PCT/EP2019/077582
§ 371 (c)(1),
(2) Date: Apr. 9, 2021

(87) PCT Pub. No.: WO2020/074699
PCT Pub. Date: Apr. 16, 2020

(65) Prior Publication Data
US 2024/0261210 A1    Aug. 8, 2024

(30) Foreign Application Priority Data
Oct. 11, 2018 (FR) ...................................... 1859442

(51) Int. Cl.
| | |
|---|---|
| *A61Q 5/10* | (2006.01) |
| *A61K 8/04* | (2006.01) |
| *A61K 8/06* | (2006.01) |
| *A61K 8/26* | (2006.01) |
| *A61K 8/58* | (2006.01) |
| *A61K 8/81* | (2006.01) |
| *A61K 8/893* | (2006.01) |
| *A61K 8/898* | (2006.01) |

(52) U.S. Cl.
CPC ............ *A61K 8/8152* (2013.01); *A61K 8/044* (2013.01); *A61K 8/064* (2013.01); *A61K 8/26* (2013.01); *A61K 8/585* (2013.01); *A61K 8/893* (2013.01); *A61K 8/898* (2013.01); *A61Q 5/10* (2013.01); *A61K 2800/884* (2013.01)

(58) Field of Classification Search
CPC ...... A61K 8/8152; A61K 8/044; A61K 8/064; A61K 8/26; A61K 8/585; A61K 8/893; A61K 8/898; A61K 2800/884; A61Q 5/10
USPC ............................................................. 8/405
See application file for complete search history.

(56) References Cited

U.S. PATENT DOCUMENTS

| | | |
|---|---|---|
| 4,578,266 A | 3/1986 | Tietjen et al. |
| 5,645,609 A | 7/1997 | Andrean et al. |
| 5,851,517 A | 12/1998 | Mougin et al. |
| 6,106,577 A | 8/2000 | Audousset et al. |
| 7,799,093 B2 | 9/2010 | Brun et al. |
| 7,862,805 B2 | 1/2011 | Mougin et al. |
| 10,071,046 B2 | 9/2018 | Portal et al. |
| 10,617,626 B2 | 4/2020 | Lion et al. |
| 10,745,582 B2 | 8/2020 | Farcet et al. |
| 2010/0183536 A1 | 7/2010 | Ansmann et al. |
| 2016/0317423 A1* | 11/2016 | Portal ................... C08F 265/06 |
| 2018/0271766 A1 | 9/2018 | Schultze et al. |
| 2018/0369127 A1* | 12/2018 | Lion ...................... A61K 8/898 |
| 2019/0000739 A1 | 1/2019 | Lion |

FOREIGN PATENT DOCUMENTS

| | | |
|---|---|---|
| CN | 108472507 A | 8/2018 |
| CN | 108472508 A | 8/2018 |
| EP | 0749747 A1 | 12/1996 |
| EP | 1184426 A2 | 3/2002 |
| EP | 2067467 A2 | 6/2009 |
| FR | 2679771 A1 | 2/1993 |
| FR | 2741530 A1 | 5/1997 |
| FR | 2907678 A1 | 5/2008 |
| FR | 3014875 A1 | 6/2015 |
| FR | 3030256 A1 | 6/2016 |
| FR | 3045363 A1 | 6/2017 |
| FR | 3045377 A1 | 6/2017 |
| FR | 3045378 A1 | 6/2017 |
| WO | 02/098377 A1 | 12/2002 |
| WO | 03/032929 A2 | 4/2003 |

(Continued)

OTHER PUBLICATIONS

Chinese Office Action for counterpart Application No. 201980067146.9, dated Oct. 26, 2022.
International Search Report and Written Opinion for counterpart Application No. PCT/EP2019/077582, dated Dec. 6, 2019.
Schlossman, Mitchell L., "Treated Pigments New Ways to Impart Color on the Skin," Cosmetics and Toiletries, vol. 105, Feb. 1990, pp. 53-64.
Translation of Japanese Office Action for JP Application No. 2021-519536, dated May 30, 2022.

*Primary Examiner* — Eisa B Elhilo

(74) *Attorney, Agent, or Firm* — THE MARBURY LAW GROUP, PLLC

(57) ABSTRACT

The disclosure relates to a process for treating keratin fibers comprising, in a first stage, the application to said fibers of an oily dispersion (A) comprising i) particles of copolymers of alkyl acrylates and anhydride acrylics, ii) stabilizers, and iii) one or more hydrocarbon-based oils, and then, in a second stage, the application to said fibers of a composition (B) comprising iv) one or more amine compounds; or the application to said fibers of an oily dispersion (D) comprising said ingredients i), ii), iii) and iv), wherein v) one or more dye(s) and/or pigment(s) may be in the dispersion (A) or (D), in a composition (B), and/or in another composition (C). The disclosure further relates to a multi-compartment kit comprising the ingredients i) to v), and an oily dispersion (A) comprising v) the one or more dyes and/or pigments.

26 Claims, No Drawings

(56) References Cited

FOREIGN PATENT DOCUMENTS

| WO | 2008/155059 | A2 | | 12/2008 | | |
|---|---|---|---|---|---|---|
| WO | 2010/046229 | A1 | | 4/2010 | | |
| WO | 2017/108593 | A1 | | 6/2017 | | |
| WO | 2017/108594 | A1 | | 6/2017 | | |
| WO | WO2017112334 | A1 | * | 6/2017 | ............... | A61Q 3/02 |

* cited by examiner

PROCESS FOR TREATING KERATIN FIBERS EMPLOYING AN ANHYDRIDE ACRYLIC POLYMER IN OILY DISPERSION AND AN AMINE COMPOUND

CROSS REFERENCE TO RELATED APPLICATION

This is a national stage application of PCT/EP2019/077582, filed internationally on Oct. 11, 2019, which claims priority to French Application No. 1859442, filed on Oct. 11, 2018, both of which are incorporated by reference herein in their entireties.

The present invention relates to a process for treating keratin fibers, notably human keratin fibers such as the hair, involving in a first stage the application to said fibers of an oily dispersion (A) comprising i) particles of copolymers of alkyl acrylates and anhydride acrylics, ii) stabilizers, iii) one or more hydrocarbon-based oils and then, in a second stage, the application to said fibers of a composition (B) comprising iv) one or more amine compounds or the application to said fibers of an oily dispersion (D) comprising said ingredients i), ii), iii) and iv), it being understood that the process of the invention involves v) one or more dye(s) and/or pigment(s) which may be in the dispersion (A) or (D) and/or in the composition (B) and/or in another composition (C). Another subject of the invention is a multi-compartment kit comprising the ingredients i) to v). Another subject of the invention is an anhydrous oily dispersion (A) comprising v) one or more dye(s) and/or pigment(s).

Cosmetic products often require the use of a film-forming polymer to obtain a deposit of the product on keratin materials that has good cosmetic properties. In particular, it is necessary for the film-forming deposit to have good persistence, in particular for the deposit not to transfer during contact with the fingers or clothing, and also good persistence on contact with water, notably rain or during showering or alternatively perspiration. Skin sebum may also damage the film-forming deposit.

In the field of dyeing keratin fibers, it is already known practice to dye keratin fibers via various techniques using direct dyes for non-permanent dyeing, or dye precursors for permanent dyeing.

Non-permanent dyeing or direct dyeing consists in dyeing keratin fibers with dye compositions containing direct dyes. These dyes are colored and coloring molecules that have affinity for keratin fibers. They are applied to the keratin fibers for a time necessary to obtain the desired coloring, and are then rinsed out.

The standard dyes that are used are, in particular, dyes of the nitrobenzene, anthraquinone, nitropyridine, azo, xanthene, acridine, azine or triarylmethane type, or natural dyes.

Some of these dyes may be used under lightening conditions, which enables the production of colorings that are visible on dark hair.

It is also known practice to dye keratin fibers permanently via oxidation dyeing. This dyeing technique consists in applying to the keratin fibers a composition containing dye precursors such as oxidation bases and couplers. Under the action of an oxidizing agent, these precursors, will form one or more colored substances in the hair.

The variety of molecules used as oxidation bases and couplers allows a wide range of colors to be obtained, and the colorings resulting therefrom are generally permanent, strong and resistant to external agents, notably to light, bad weather, washing, perspiration and rubbing.

In order to be visible on dark hair, these two dyeing techniques require prior or simultaneous bleaching of the keratin fibers. This bleaching step, performed with an oxidizing agent such as hydrogen peroxide or persalts, results in appreciable degradation of the keratin fibers, which impairs their cosmetic properties. The hair then has a tendency to become coarse, more difficult to disentangle and more brittle.

Another dyeing method consists in using pigments. Specifically, the use of pigment on the surface of keratin fibers generally makes it possible to obtain colorings visible on dark hair, since the surface pigment masks the natural color of the fiber. The use of pigment for dyeing keratin fibers is described, for example, in patent application FR 2 741 530, which recommends using, for the temporary dyeing of keratin fibers, a composition comprising at least one dispersion of film-forming polymer particles including at least one acid function and at least one pigment dispersed in the continuous phase of said dispersion.

The colorings obtained via this dyeing method have the drawback of being removed from the very first shampoo wash.

It is moreover known practice from patent application FR 2 907 678 to perform colored coatings of the hair using a composition comprising a polysiloxane/polyurea block copolymer and a pigment. However, with such a composition, the coatings obtained are not always very homogeneous and the individualization of the hair strands is not always very good.

It is also known practice from patent EP 1 392 222 to use a cosmetic composition for caring for and/or treating keratin materials, comprising a supramolecular polymer including a polymer backbone and at least two groups that are capable of forming at least three hydrogen bonds, and from patent EP 1 435 900 to use a hair composition comprising a supramolecular polymer including a polymer backbone and at least two groups that are capable of forming at least three hydrogen bonds and a surfactant or a hair-conditioning agent.

It is also known practice to use, in other cosmetic fields, dispersions of polymer particles of nanometric size, in organic media such as hydrocarbon-based oils. Polymers are notably used as film-forming agents in makeup products such as mascaras, eyeliners, eyeshadows or lipsticks. EP-A-749 747 describes in the examples dispersions in hydrocarbon-based oils (liquid paraffin, isododecane) of acrylic polymers stabilized with polystyrene/copoly(ethylene-propylene) diblock copolymers. The film obtained after application of the dispersion to the skin is sparingly glossy. FR 3 014 875 also describes the use of dispersions of surface-stabilized polymer particles containing hydrocarbon-based oils for making up the lips and eyelashes. WO-A-2010/046229 describes dispersions in isododecane of acrylic polymers stabilized with stabilizing polymers.

Thus, the aim of the present invention is to provide a method for treating keratin fibers that has good resistance to attacking factors such as brushing, does not leach, is resistant to sweat, light and bad weather, and is fast with respect to shampoo washing and to the various attacking factors to which said fibers may be subjected, without degrading said fibers, and while keeping the keratin fibers perfectly individualized.

The technical problem has been solved by the process of the invention, which is a process for treating keratin fibers, notably human keratin fibers such as the hair, comprising:
 1a) the application to said fibers of an oily dispersion (A), which is preferably anhydrous, comprising:
  i) one or more particle(s) constituted of one or more ethylenic copolymer(s):

a) of $(C_1-C_4)$alkyl $(C_1-C_4)$(alkyl)acrylate, and
b) of ethylenically unsaturated anhydride compound; and ii) one or more stabilizer(s) constituted of ethylenic polymers chosen from:

c) polymers of $(C_3-C_{12})$cycloalkyl $(C_1-C_6)$(alkyl) acrylate monomers; and
d) copolymers of $(C_3-C_{12})$cycloalkyl $(C_1-C_6)$(alkyl) acrylate and $(C_1-C_4)$alkyl $(C_1-C_4)$(alkyl)acrylate; and iii) one or more hydrocarbon-based oil(s), followed by 1b) the application to said fibers of a composition (B) comprising:

iv) one or more amine compound(s) chosen from:

e) polyamine compounds bearing several primary amine and/or secondary amine groups, and
f) amino alkoxysilanes; or 2) the application to said fibers of an oily dispersion (D), which is preferably anhydrous, comprising said ingredients i), ii), iii) and iv);

it being understood that the process of the invention involves v) one or more dye(s) and/or pigment(s) which are:
in the dispersion (A) or (D); and/or
in the composition (B); and/or
in another composition (C), said composition (C) is applied to said fibers.

This process for treating keratin fibers makes it possible to obtain a treatment of said fibers that is resistant notably to shampoo washes and to water.

The process in accordance with the present invention makes it possible notably to obtain on the keratin fibers coatings, in particular colored coatings, having visible coloring on all types of fibers, notably on dark hair, in a manner which persists after shampoo washing, while at the same time preserving the physical qualities of the keratin fiber. Such a coating is, in particular, resistant to the external attacking factors to which the hair may be subjected, such as blow-drying and perspiration. It makes it possible in particular to obtain a smooth and uniform deposit. Moreover, it has been observed, surprisingly, that the keratin fibers remained perfectly individualized, and could be styled without any problem.

The term "individualized keratin fibers" means keratin fibers, notably hair, which, after application of the composition and drying, are not stuck together (or are all separate from each other) and therefore do not form clumps of fibers, since the coating is formed around virtually every fiber.

For the purposes of the present invention and unless otherwise indicated:

an "alkyl radical" is a linear or branched saturated $C_1-C_8$, in particular $C_1-C_6$, preferably $C_1-C_4$ hydrocarbon-based group such as methyl, ethyl, isopropyl and tert-butyl;

an "alkylene radical" is a linear or branched divalent saturated $C_1-C_8$, in particular $C_1-C_6$, preferably $C_1-C_4$ hydrocarbon-based group such as methylene, ethylene or propylene;

a "cycloalkyl" radical is a cyclic saturated hydrocarbon-based group comprising from 1 to 3 rings, preferably 2 rings, and comprising from 3 to 13 carbon atoms, preferably between 5 and 10 carbon atoms, such as cyclopentyl, cyclohexyl, cycloheptyl, norbornyl, or isobornyl, the cycloalkyl radical possibly being substituted with one or more $(C_1-C_4)$alkyl groups such as methyl; preferably, the cycloalkyl group is an isobornyl group.

a "cyclic" radical is a cyclic saturated or unsaturated, aromatic or non-aromatic hydrocarbon-based group comprising from 1 to 3 rings, preferably 1 ring, and comprising from 3 to 10 carbon atoms, such as cyclohexyl or phenyl;

an "aryl" radical is a cyclic unsaturated aromatic radical comprising from 6 to 12 carbon atoms, which is mono- or bicyclic, fused or unfused; preferably, the aryl group comprises 1 ring comprising 6 carbon atoms, such as phenyl;

an "aryloxy" radical is an aryl-oxy, i.e. aryl-O—, radical, with aryl as defined previously, preferably phenoxy;

an "aryl$(C_1-C_4)$alkoxy" radical is an aryl-$(C_1-C_4)$alkyl-O— radical, preferably benzoxy;

the term "keratin fibers" particularly means human keratin fibers such as head hair, eyelashes, eyebrows, and bodily hair, preferentially head hair, eyebrows and eyelashes, even more preferentially head hair.

The Oily Dispersion (A)

According to a preferred embodiment, the process of the invention involves at least one oily dispersion (A) of i) particles of at least one polymer surface-stabilized with ii) at least one stabilizer in a preferably anhydrous medium, further containing iii) at least one hydrocarbon-based oil.

Moreover, the dispersions according to the invention are constituted of particles, which are generally spherical, of at least one surface-stabilized polymer, in a non-aqueous medium.

i) Polymer Particles

The particle(s) of the dispersion of the process of the invention are constituted of one or more ethylenic copolymer(s) of a) $(C_1-C_4)$alkyl $(C_1-C_4)$(alkyl)acrylate and of b) an ethylenically unsaturated anhydride compound.

The term "ethylenic copolymer" means a polymer resulting from the polymerization of two monomers: of the monomer a) $(C_1-C_4)$alkyl $(C_1-C_4)$(alkyl)acrylate and of the monomer b) of ethylenically unsaturated anhydride compound.

The term "ethylenically unsaturated anhydride compound" means a carboxylic acid anhydride compound comprising at least one ethylenic unsaturation —$(R_a)$C=C$(R_b)$—, —C$(R_a)$=C$(R_b)$—$R_c$ or >C=C$(R_a)$—$R_b$, with $R_a$, $R_b$, and $R_c$, which may be identical or different, representing a hydrogen atom or a $(C_1-C_4)$alkyl group such as methyl, preferably hydrogen. In particular, the ethylenically unsaturated anhydride compound is a cyclic compound, which is preferably 5- or 6-membered, and comprising an ethylenic unsaturation.

According to a preferred embodiment of the invention, the polymer constituting the particles i) is a copolymer of acrylate:

a) of formula $H_2C$=C(R)—C(O)—O—R' with R representing a hydrogen atom or a $(C_1-C_4)$alkyl group such as methyl, and R' representing a $(C_1-C_4)$alkyl group such as methyl or ethyl, preferably $C_1-C_4$ alkyl (meth) acrylate; and
b) of an ethylenically unsaturated anhydride monomer.

Particularly, the polymer of the particles is a polymer of $C_1-C_4$ alkyl (meth)acrylate and of ethylenically unsaturated anhydride monomer.

The monomers a) are preferably chosen from methyl (meth)acrylate, ethyl (meth)acrylate, n-propyl (meth)acrylate, isopropyl (meth)acrylate, n-butyl (meth)acrylate and tert-butyl (meth)acrylate.

A $C_1-C_4$ alkyl acrylate monomer is advantageously used. Preferentially, a) is chosen from methyl acrylate and ethyl acrylate.

The polymer of the particles also comprises an ethylenically unsaturated anhydride monomer b).

Preferentially, the ethylenically unsaturated anhydride compound(s) b) of the invention are chosen from derivatives of maleic anhydride (Ib) and itaconic anhydride (IIb):

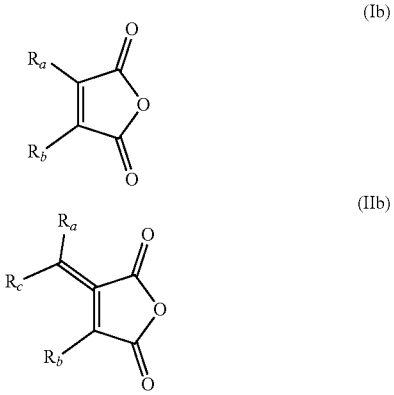

in which formulae (Ib) and (IIb) $R_a$, $R_b$ and $R_c$, which may be identical or different, represent a hydrogen atom or a $(C_1-C_4)$alkyl group; preferably, $R_a$, $R_b$, and $R_c$ represent a hydrogen atom.

More preferentially, the ethylenically unsaturated anhydride monomer of the invention is of formula (Ib) and even more preferentially is maleic anhydride.

According to a preferred embodiment of the invention, the polymer(s) of the particles comprise, or essentially consist of, from 80 to 99.99% by weight of monomer a) and from 0.01 to 20% by weight of monomer b), relative to the total weight of the polymer.

The polymer of the particles may be chosen from:

methyl acrylate/maleic anhydride copolymers;

ethyl acrylate/maleic anhydride copolymers; and methyl acrylate/ethyl acrylate/maleic anhydride copolymers.

Advantageously, the polymer of the particles is a non-crosslinked polymer.

The polymer of the particles of the dispersion preferably has a number-average molecular weight ranging from 2000 to 10 000 000.

The polymer of the particles may be present in the dispersion in an amount ranging from 20% to 60% by weight relative to the total weight of the dispersion (A), in particular between 21% and 58.5% by weight relative to the total weight of the dispersion (A), preferably ranging from 30% to 50% by weight relative to the total weight of the dispersion (A), more preferentially ranging from 36% to 42% by weight relative to the total weight of the dispersion (A).

ii) The Stabilizer(s)

The dispersion (A) according to the invention also comprises one or more stabilizers ii). Preferably, a single type of stabilizer ii) is used in the invention.

The stabilizer(s) of the invention are constituted of ethylenic polymers chosen from c) polymers of $(C_3-C_{12})$cycloalkyl $(C_1-C_6)$(alkyl)acrylate monomers; and d) copolymers of $(C_3-C_{12})$cycloalkyl $(C_1-C_6)$(alkyl)acrylate and $(C_1-C_4)$alkyl $(C_1-C_4)$(alkyl)acrylate.

According to a preferred embodiment of the invention, the stabilizer ii) is constituted of ethylenic polymers chosen from
  c) polymers of monomers of formula $H_2C=C(R)-C(O)-O-R''$ with R representing a hydrogen atom or $(C_1-C_4)$alkyl group such as methyl, and R'' representing a $(C_5-C_{10})$cycloalkyl group such as norbornyl or isobornyl, preferably isobornyl; and
  d) copolymers of $H_2C=C(R)-C(O)-O-R'$ and of $H_2C=C(R)-C(O)-O-R''$ with R, R' and R'' as defined previously.

Particularly, the stabilizer ii) is an isobornyl (meth)acrylate polymer chosen from isobornyl (meth)acrylate homopolymer and statistical copolymers of isobornyl (methacrylate and $C_1-C_4$ alkyl (meth)acrylate which are preferably present in an isobornyl (meth)acrylate/$C_1-C_4$ alkyl (meth)acrylate weight ratio of greater than 4. Advantageously, said weight ratio ranges from 4.5 to 19.

For these statistical copolymers, the defined weight ratio makes it possible to obtain a polymer dispersion that is stable, notably after storage for seven days at room temperature.

Advantageously, the stabilizer is chosen from:
  isobornyl acrylate homopolymers,
  statistical copolymers of isobornyl acrylate/methyl acrylate,
  statistical copolymers of isobornyl acrylate/ethyl acrylate; and
  statistical copolymers of isobornyl acrylate/methyl acrylate/ethyl acrylate according to the weight ratio described previously.

Advantageously, the sum of ii) stabilizer(s)+i) particle(s) of polymer(s) present in the dispersion (A) comprises from 10 to 50% by weight of copolymers d) and from 50 to 90% by weight of polymers c), relative to the total weight of the sum of ii) stabilizer(s)+i) particle(s) of polymer(s).

Preferentially, the sum of ii) stabilizer(s)+i) polymer particle(s) present in the dispersion comprises from 15 to 30% by weight of copolymers d) and from 70 to 85% by weight of polymers c), relative to the total weight of the sum of ii) stabilizer(s)+i) polymer particle(s).

iii) The Hydrocarbon-Based Oil(s)

The dispersion (A) according to the invention comprises one or more identical or different, preferably identical, hydrocarbon-based oils.

The term "oil" means a fatty substance that is liquid at room temperature (25° C.) and at atmospheric pressure.

The term "hydrocarbon-based oil" means an oil formed essentially from, or even constituted of, carbon and hydrogen atoms, and optionally oxygen and nitrogen atoms, and not containing any silicon or fluorine atoms. It may contain hydroxy, ester, ether, carboxylic acid, amine and/or amide groups.

The hydrocarbon-based oil may be volatile or nonvolatile.

According to a preferred embodiment of the invention, the hydrocarbon-based oil(s) are volatile or are a mixture of different volatile oils, more preferentially chosen from isododecane and octyldodecanol.

According to another particular embodiment, the hydrocarbon-based oil(s) are a mixture of a volatile oil and a nonvolatile oil.

The term "volatile oil" refers to an oil (or non-aqueous medium) that can evaporate on contact with the skin in less than one hour, at room temperature and at atmospheric pressure. The volatile oil is a volatile cosmetic oil, which is liquid at room temperature, notably having a nonzero vapor pressure, at room temperature and at atmospheric pressure, in particular having a vapor pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.01 to 10 mmHg).

The term "nonvolatile oil" refers to an oil with a vapor pressure of less than 0.13 Pa.

Volatile silicone oils that may be mentioned include volatile linear or cyclic silicone oils, notably those with a viscosity ≤8 centistokes (cSt) ($8\times10^{-6}$ m$^2$/s), and notably containing from 2 to 10 silicon atoms and in particular from 2 to 7 silicon atoms, these silicones optionally including alkyl or alkoxy groups containing from 1 to 10 carbon atoms. As volatile silicone oils that may be used in the invention, mention may be made in particular of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As nonvolatile silicone oils, mention may be made of linear or cyclic nonvolatile polydimethylsiloxanes (PDMSs); polydimethylsiloxanes including alkyl, alkoxy and/or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates and pentaphenyl silicone oils.

The hydrocarbon-based oil may be chosen from:
  hydrocarbon-based oils containing from 8 to 14 carbon atoms, and notably:
    branched $C_8$-$C_{14}$ alkanes, for instance $C_5$-$C_{14}$ isoalkanes of petroleum origin (also known as isoparaffins), for instance isododecane (also known as 2,2,4,4,6-pentamethylheptane), isodecane and, for example, the oils sold under the trade names Isopar or Permethyl,
    linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in examples 1 and 2 of patent application WO 2008/155 059 from the company Cognis, and mixtures thereof,
    short-chain esters (containing from 3 to 8 carbon atoms in total) such as ethyl acetate, methyl acetate, propyl acetate or n-butyl acetate,
    hydrocarbon-based oils of plant origin such as triglycerides constituted of fatty acid esters of glycerol, the fatty acids of which may have chain lengths varying from $C_4$ to $C_{24}$, these chains possibly being linear or branched, and saturated or unsaturated; these oils are notably heptanoic or octanoic acid triglycerides, or alternatively wheatgerm oil, sunflower oil, grapeseed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, sesame oil, marrow oil, rapeseed oil, blackcurrant oil, evening primrose oil, millet oil, barley oil, quinoa oil, rye oil, safflower oil, candlenut oil, passionflower oil and musk rose oil; shea butter; or else caprylic/capric acid triglycerides, for instance those sold by the company Stéarineries Dubois or those sold under the names Miglyol 810®, 812® and 818® by the company Dynamit Nobel,
  synthetic ethers containing from 10 to 40 carbon atoms;
  linear or branched hydrocarbons of mineral or synthetic origin, such as petroleum jelly, polydecenes, hydrogenated polyisobutene such as Parleam®, squalane and liquid paraffins, and mixtures thereof,
  synthetic esters such as oils of formula $R_1C(O)$—O—$R_2$ in which $R_1$ represents a linear or branched fatty acid residue including from 1 to 40 carbon atoms and $R_2$ represents an, in particular branched, hydrocarbon-based chain containing from 1 to 40 carbon atoms, on the condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters,
  fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

The dispersion (A), in addition to the hydrocarbon-based oil, may comprise a silicone oil. If silicone oil is in the dispersion (A), it is preferably in an amount which does not exceed 10% by weight relative to the weight of the dispersion (A), more particularly in an amount of less than 5% and more preferentially 2%. The term "silicone oil" means an oil comprising at least one silicon atom and notably at least one Si—O group. The silicone oil may be volatile or nonvolatile.

According to a particular embodiment, the dispersion (A) comprises a hydrocarbon-based oil in a content ranging from 60 to 100% by weight of the total weight of the oils present in the composition and from 0 to 40% by weight of silicone oil. According to a preferred embodiment of the invention, the composition contains as oil only a hydrocarbon-based oil.

Advantageously, the hydrocarbon-based oils of the invention are apolar, i.e. formed solely of carbon and hydrogen atoms.

The hydrocarbon-based oils are preferably chosen from hydrocarbon-based oils containing from 8 to 14 carbon atoms, which are in particular volatile, more particularly the apolar oils, described previously.

Preferentially, the hydrocarbon-based oil(s) of the invention are isododecane.

According to another advantageous embodiment of the invention, the hydrocarbon-based oil(s) are a mixture of nonvolatile and volatile oil; preferably, the mixture comprises isododecane as volatile oil. In particular, in the mixture, the nonvolatile oil is a phenyl silicone oil, preferably chosen from pentaphenyl silicone oils.

According to a particular embodiment of the invention, the compositions used in the process, (B) and (C), also comprise at least one oil as defined previously, notably a hydrocarbon-based oil.

The polymer particles of the dispersion preferably have a number-average size ranging from 5 to 500 nm, notably ranging from 10 to 400 nm and better still ranging from 20 to 300 nm.

Method for Preparing the Dispersion (A)

Without this being limiting, in general, the dispersion according to the invention may be prepared in the following manner:

The polymerization is performed in "dispersion", i.e. by precipitation of the polymer being formed, with protection of the particles formed with one or more stabilizers, preferably one stabilizer.

In a first step, the stabilizing polymer (or stabilizer ii)) is prepared by mixing the constituent monomer(s) of the stabilizing polymer c) or d) with iv) a free-radical initiator, in a solvent known as the synthesis solvent, and by polymerizing these monomers;

In a second step, the constituent monomers of the polymer of the particles i) are added to the stabilizing polymer formed in the preceding step and polymerization of these added monomers is performed in the presence of the free-radical initiator.

When the nonaqueous medium is a nonvolatile hydrocarbon-based oil iii), the polymerization may be performed in an apolar organic solvent (synthesis solvent), followed by adding the nonvolatile hydrocarbon-based oil (which should be miscible with said synthesis solvent) and selectively distilling off the synthesis solvent.

The dye(s) and/or pigment(s) may be added during the first step. According to another variant, the dye(s) and/or pigment(s) are added during the second step or after the second step.

A synthesis solvent which is such that the monomers of the stabilizing polymer and the free-radical initiator are soluble therein, and the polymer particles obtained are insoluble therein, so that they precipitate therein during their formation, is thus chosen.

In particular, the synthesis solvent is chosen which is apolar and organic, preferably chosen from alkanes such as heptane or cyclohexane.

When the nonaqueous medium is a volatile hydrocarbon-based oil iii), the polymerization may be performed directly in said oil, which thus also acts as synthesis solvent. The monomers should also be soluble therein, as should the free-radical initiator, and the polymer of the particles which is obtained should be insoluble therein.

The monomers are preferably present in the synthesis solvent, before polymerization, in a proportion of 5% to 45% by weight. The total amount of the monomers may be present in the solvent before the start of the reaction, or part of the monomers may be added gradually as the polymerization reaction proceeds.

The polymerization is preferentially performed in the presence vi) of one or more free-radical initiators, notably of the type such as:
peroxide, in particular chosen from tert-butyl peroxy-2-ethylhexanoate: Trigonox 21S; 2,5-dimethyl-2,5-bis(2-ethylhexanoylperoxy)hexane: Trigonox 141; tert-butyl peroxypivalate: Trigonox 25C75 from AkzoNobel; or
azo, in particular chosen from AIBN: azobisisobutyronitrile; V50: 2,2'-azobis(2-amidinopropane) dihydrochloride.

The polymerization is preferably performed at a temperature ranging from 70 to 110° C. and at atmospheric pressure.

The polymer particles i) are surface-stabilized, when they are formed during the polymerization, by means of the stabilizer ii).

The stabilization may be performed by any known means, and in particular by direct addition of the stabilizer ii), during the polymerization.

The stabilizer ii) is preferably also present in the mixture before polymerization of the monomers of the polymer of the particles i). However, it is also possible to add it continuously, notably when the monomers of the polymer of the particles i) are also added continuously.

From 10% to 30% by weight and preferably from 15% to 25% by weight of the stabilizer(s) may be used relative to the total weight of monomers used (stabilizers ii)+polymer particles i)).

The polymer particle dispersion (A) advantageously comprises from 30% to 65% by weight of solids relative to the total weight of said dispersion and preferably from 40% to 60% by weight relative to the total weight of said dispersion.

The dispersion (A) according to the invention preferably comprises a content of polymers of particle i)+dispersing polymers ii) ranging from 1% to 50% by weight, preferably ranging from 2% to 30% by weight, relative to the total weight of the dispersion (A).

According to a preferred embodiment of the invention, the dispersion (A) according to the invention is an anhydrous composition.

The term "anhydrous" dispersion or composition refers to a dispersion or composition containing less than 2% by weight of water, or even less than 0.5% of water, and notably free of water. Where appropriate, such small amounts of water may notably be introduced by ingredients of the composition that may contain residual amounts thereof.

According to another embodiment of the present patent application, the dispersion (A) is in inverse emulsion, i.e. of water-in-oil type (W/O). In this case, the composition comprises one or more surfactants, which are preferably nonionic. The inverse emulsions of (A) are preferably chosen in makeup, notably of the eyelashes and eyebrows.

The Composition (B)

Composition (B) of the process of the invention comprises one or more amine compounds iv).

iv) The Amine Compound(s):

The amine compounds used in the process of the invention are chosen from:
e) polyamines bearing several primary amine and/or secondary amine groups, and
f) amino alkoxysilanes.

The amine compound(s) used in the process according to the invention are notably chosen from amino alkoxysilane compounds, diamine compounds and triamine compounds.

According to a particular embodiment of the invention, the polyamine compound(s) particularly comprise from 2 to 20 carbon atoms; the polyamine compound(s) are notably non-polymeric.

The term "non-polymeric" compound(s) refers to one or more compounds which is or are not directly obtained via a monomer polymerization reaction.

Polyamine compounds that may notably be mentioned include N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenediamine, 1,4-butylenediamine, lysine, cystamine, xylenediamine, tris(2-aminoethyl)amine and spermidine.

According to another particular embodiment of the invention, the amine compound(s) iv) are chosen from f) amino alkoxysilanes such as those of formula (IVa):

in which formula (IVa):
- $R'_1$ is a linear or branched, saturated or unsaturated, cyclic or acyclic $C_1$-$C_{10}$ hydrocarbon-based chain substituted with one or more groups chosen from the groups:
  - primary amine $NH_2$ or secondary amine $N(H)R$ with R representing a $(C_1$-$C_4)$alkyl group,
  - aryl or aryloxy substituted with an amino or $(C_1$-$C_4)$ alkylamino group or with a $C_1$-$C_4$ aminoalkyl group, and
  - aldehyde —C(O)—H, carboxy —C(O)—OH, amide —C(O)—$NH_2$ or urea-NH—C(O)—$NH_2$; $R'_1$ is optionally interrupted in its hydrocarbon-based chain with one or more heteroatoms (notably O, S, NH), a carbonyl group (CO), or the combination thereof, such as ester —C(O)—O—, or amide —C(O)—NH—, R' being bonded directly to the silicon atom via a carbon atom,
- $R'_2$ and $R'_3$ which may be identical or different, represent a linear or branched alkyl group comprising from 1 to 6 carbon atoms,
- z denotes an integer ranging from 1 to 3,
- and x denotes an integer ranging from 0 to 2, with z+x=3.

Preferably, $R'_2$ represents an alkyl group comprising from 1 to 4 carbon atoms.

Preferably, $R'_2$ represents a linear alkyl group, comprising from 1 to 4 carbon atoms.

Preferably, $R'_2$ represents an ethyl group.

Preferably, $R'_3$ represents an alkyl group comprising from 1 to 4 carbon atoms.

Preferably, $R'_3$ represents a linear alkyl group, comprising from 1 to 4 carbon atoms.

Preferably, $R'_3$ represents a methyl or ethyl group.

Preferably, $R'_3$ is an acyclic chain.

Preferably, $R'_1$ is a linear or branched, saturated or unsaturated $C_1$-$C_6$ hydrocarbon-based chain substituted with an amine $NH_2$ or $N(H)R$ group, with R representing a $C_1$-$C_6$ alkyl, $C_3$-$C_6$ cycloalkyl, or $C_6$ aromatic group.

Preferentially, $R'_1$ is a saturated linear $C_1$-$C_6$ hydrocarbon-based chain substituted with an amine group $NH_2$.

More preferentially, $R'_1$ is a saturated linear $C_2$-$C_6$ hydrocarbon-based chain substituted with an amine group $NH_2$.

Preferably. $R'_1$ is a saturated linear $C_1$-$C_6$ hydrocarbon-based chain substituted with an amine group $NH_2$.

$R'_2$ represents an alkyl group comprising from 1 to 4 carbon atoms, $R'_3$ represents an alkyl group comprising from 1 to 4 carbon atoms.

Preferably, z is equal to 3.

Preferably, the amino alkoxysilane of formula (IVa) is chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane and N-(2-aminoethylaminomethyl)phenethyltrimethoxysilane.

Preferably, the amino alkoxysilane (IVa) is chosen from 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane.

Preferably, the amino alkoxysilane (IVa) is 3-aminopropyltriethoxysilane (APTES).

Preferably, the amine compound(s) are chosen from 3-aminopropyltriethoxysilane (APTES), N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenediamine, 1,4-butylenediamine and lysine.

Preferentially, the amine compound is chosen from ethylenediamine, 1,3-propylenediamine, 1,4-butylenediamine and 3-aminopropyltriethoxysilane (APTES).

More preferentially, the amine compound is ethylenediamine or 3~ aminopropyltriethoxysilane (APTES).

The amine compound(s) may also be chosen from e) polyamines bearing several primary amine and/or secondary amine groups and in particular amine polymers, notably having a weight-average molecular weight ranging from 500 to 1 000 000, preferably ranging from 500 to 500 000, and preferentially ranging from 500 to 100 000.

As amine or polyamine polymers e), use may be made of poly(($C_2$-$C_5$)alkyleneimines), and in particular:
- polyethyleneimines and polypropyleneimines, notably poly(ethyleneimine)s (for example the product sold under the reference 46,852-3 by the company Aldrich Chemical);
- poly(allylamine) (for example the product sold under the reference 47.913-6 by the company Aldrich Chemical);
- polyvinylamines and copolymers thereof, in particular with vinylamides; mention may notably be made of vinylamine/vinylformamide copolymers, such as those sold under the name Lupamin® 9030 by the company BASF;
- polyamino acids containing $NH_2$ groups such as polylysine, for example the product sold by the company JNC Corporation (formerly Chisso); aminodextran, such as the product sold by the company CarboMer Inc;
- amino polyvinyl alcohol, such as the product sold by the company CarboMer Inc, copolymers based on acrylamidopropylamine;
- chitosans; and
- polydi($C_1$-$C_4$)alkylsiloxanes, in particular polydimethylsiloxanes, comprising amine groups at the chain end or on side chains are particularly end or side amino($C_1$-$C_6$)alkyl groups such as aminopropyl, more particularly those of formula (IVb) or (IVc) or (IVd):

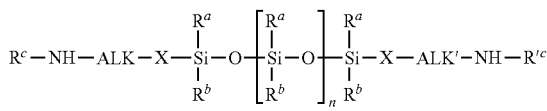

in which formula (IVb) $R^a$ and $R^b$, which may be identical or different, preferably identical, represent a $(C_1$-$C_4)$alkyl group such as methyl, $(C_1$-$C_4)$alkoxy such as methoxy, aryl such as phenyl, aryloxy such as phenoxy, aryl$(C_1$-$C_4)$alkyl such as benzyl, or aryl$(C_1$-$C_4)$alkoxy such as benzoxy, preferably $(C_1$-$C_4)$alkyl such as methyl, $R^c$ and $R'^c$, which may be identical or different, preferably identical, represent a hydrogen atom, a $(C_1$-$C_4)$alkyl group, an amino ($C_1$-$C_4$)alkyl or ($C_1$-$C_4$)alkylamino($C_1$-$C_4$)alkyl group, preferably a hydrogen atom or an amino($C_1$-$C_4$)alkyl group such as aminoethyl; X represents a covalent bond, an oxygen atom, preferably a covalent bond; ALK and ALK', which may be identical or different, preferably identical, represent a ($C_1$-$C_6$) alkylene group, preferably ($C_1$-$C_4$)alkylene such as propylene; n representing an integer greater than 2 and more particularly the value of n is such that the weight-average molecular weight of the silicone is between 500 and 55 000;

Preferentially, the polydi($C_1$-$C_4$)alkylsiloxanes of formula (IVb) are of formula (IV'b) below:

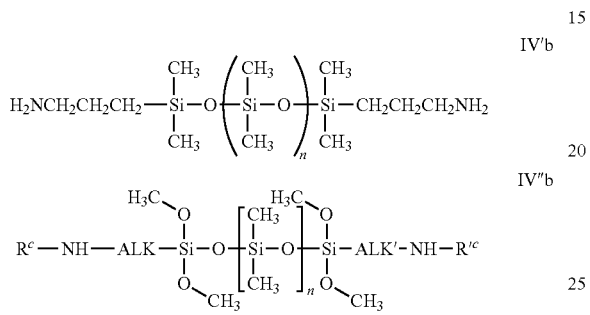

in which formula (IVb) the value of n is such that the weight-average molecular weight of the silicone is between 500 and 55 000. As an example of aminosilicone (IVb) or (IV'b), mention may be made of those sold under the names DMS-A11, DMS-A12, DMS-A15, DMS-A21, DMS-A31, DMS-A32 and DMS-A35 by the company Gelest;

formula (IV''b) with $R^c$, $R^{Ic}$, ALK, ALK', and n as defined previously for (IVb).

Preferably, ALK and ALK' are identical and represent a ($C_1$-$C_4$)alkylene group such as propylene, $R^c$ and $R^{Ic}$ are identical and represent an amino($C_1$-$C_6$)alkyl group such as aminoethyl mention may be made particularly of Dimethoxysilyl Ethylenediaminopropyl Dimethicone (RN: 71750-80-6), under the trade name GP-RA-157, sold by Genesee Polymers.

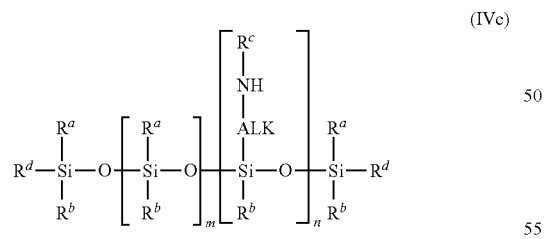

in which formula (IVc) $R^a$, $R^b$, and $R^d$, which may be identical or different, preferably identical, represent a ($C_1$-$C_4$)alkyl group such as methyl, ($C_1$-$C_4$)alkoxy such as methoxy, aryl such as phenyl, aryloxy such as phenoxy, aryl($C_1$-$C_4$)alkyl such as benzyl, or aryl($C_1$-$C_4$)alkoxy such as benzoxy, preferably ($C_1$-$C_4$)alkyl such as methyl, $R^d$ may also represent a ($C_1$-$C_6$)alkyl group substituted with a ($C_1$-$C_4$)alkylamino or amino group, $R^c$ represents a hydrogen atom or a ($C_1$-$C_4$)alkyl group, preferably a hydrogen atom; ALK represents a ($C_1$-$C_6$)alkyl group, preferably ($C_1$-$C_4$)alkylene such as propylene; n and m, which may be identical or different, represent an integer greater than 2 and more particularly the values of m and n are such that the weight-average molecular weight of the silicone is between 1000 and 55 000;

Preferentially, the polydi($C_1$-$C_4$)alkylsiloxanes of formula (IVc) have the formula (IV'c) below:

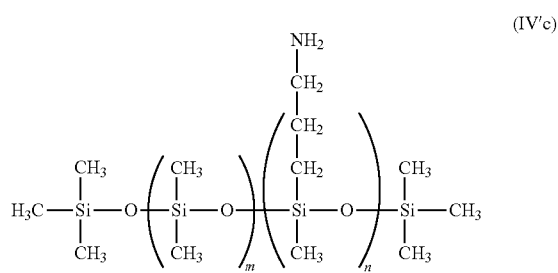

in which formula (IVc) the values of n and m are such that the weight-average molecular weight of the silicone is between 1000 and 55 000. As examples of silicone (IVc), mention may be made of those sold under the names AMS-132, AMS-152, AMS-162, AMS-163, AMS-191 and AMS-1203 by the company Gelest;

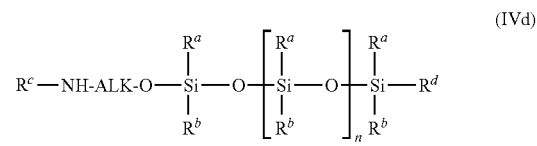

in which formula (IVd) $R^a$ and $R^b$, which may be identical or different, preferably identical, represent a ($C_1$-$C_4$)alkyl group such as methyl, ($C_1$-$C_4$)alkoxy such as methoxy, aryl such as phenyl, aryloxy such as phenoxy, aryl($C_1$-$C_4$)alkyl such as benzyl, or aryl($C_1$-$C_4$)alkoxy such as benzoxy, preferably ($C_1$-$C_4$)alkyl such as methyl, and $R^d$ represents a ($C_1$-$C_6$)alkyl group optionally substituted with a ($C_1$-$C_4$) alkylamino or amino group, preferably ($C_1$-$C_4$)alkyl, such as isobutyl, tert-butyl or n-butyl, $R^c$ represents a hydrogen atom or a ($C_1$-$C_4$)alkyl group, preferably a hydrogen atom; ALK represents a ($C_1$-$C_6$)alkylene group, preferably ($C_1$-$C_4$)alkylene such as propylene, n representing an integer greater than 2 and more particularly the value of n is such that the weight-average molecular weight of the silicone is between 500 and 5000;

Preferentially, the polydi($C_1$-$C_4$)alkylsiloxanes of formula (IVc) have the formula (IV c) below:

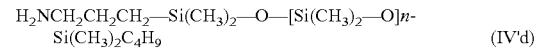

in formula (IV'd), the value of n is such that the weight-average molecular weight of the silicone is between 500 and 3000. As examples of silicones (IVd), mention may be made of the products sold under the names MCR-A11 and MCR-A12 by the company Gelest:

the amodimethicones of formula (IVe):

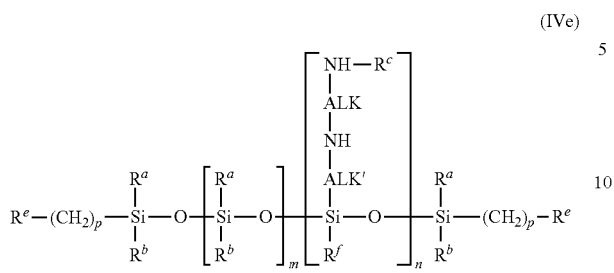

(IVe)

in which formula (IVe)
- $R^a$ and $R^b$, which may be identical or different, preferably identical, represent a ($C_1$-$C_4$)alkyl group such as methyl, ($C_1$-$C_4$)alkoxy such as methoxy, aryl such as phenyl, aryloxy such as phenoxy, aryl($C_1$-$C_4$)alkyl such as benzyl, or aryl($C_1$-$C_4$)alkoxy such as benzoxy, preferably ($C_1$-$C_4$)alkyl such as methyl,
- $R^c$ represents a hydrogen atom or a ($C_1$-$C_4$)alkyl group, preferably a hydrogen atom;
- $R^e$ represents a hydroxyl, ($C_1$-$C_4$)alkoxy, amino or ($C_1$-$C_4$)alkylamino group,
- $R^f$ represents a ($C_1$-$C_4$)alkyl group such as methyl, ($C_1$-$C_4$)alkoxy such as methoxy, a hydroxyl group or —O—$(SiR_2)_x$—R' with R representing a ($C_1$-$C_4$)alkyl or ($C_1$-$C_4$)alkoxy group and R' representing a ($C_1$-$C_4$)alkoxy or hydroxyl group; preferably, $R^f$ represents a ($C_1$-$C_4$)alkyl, ($C_1$-$C_4$)alkoxy or —O—$(SiR_2)_x$—R' group with R representing a ($C_1$-$C_4$)alkyl group such as methyl and R' a hydroxyl or ($C_1$-$C_4$)alkoxy group such as methoxy;
- $R^g$ represents a hydrogen atom or a ($C_1$-$C_6$)alkyl group
- ALK and ALK', which may be identical or different, represent a ($C_1$-$C_6$)alkylene group, preferably ($C_1$-$C_4$)alkylene such as ethylene or propylene; n and m, which may be identical or different, represent an integer greater than 2, p and x are integers greater than or equal to 0; preferably, p is between 2 and 20 and more particularly the values of m, n, p and x are such that the weight-average molecular weight of the silicone is between 2000 and 700 000, preferentially between 5000 and 500 000;

Preferentially, the amodimethicones of formula (IVe) are of formula (IV'e) below:

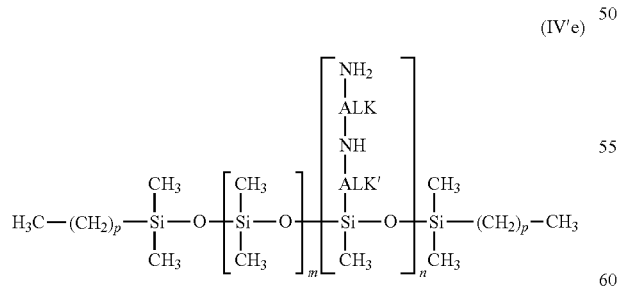

(IV'e)

in which formula (IV'e) ALK represents a ($C_1$-$C_6$) alkylene group, preferably ethylene, ALK' represents a ($C_1$-$C_6$)alkylene group, preferably propylene, and m, n and p which may be identical or different, represent an integer greater than 2, with m, n and p such that the weight-average molecular weight of the compound is between approximately 5000 and 500 000; preferably, p represents an integer of between 8 and 20;

according to another preferred embodiment, the amodimethicones of formula (IVe) are chosen from those of formula

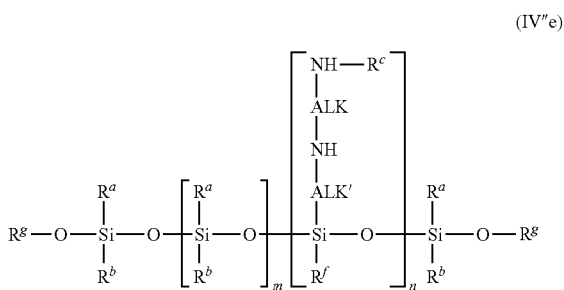

(IV"e)

in which formula (IV"e)
- $R^a$ and $R^b$, which may be identical or different, preferably identical, represent a ($C_1$-$C_4$)alkyl group such as methyl, ($C_1$-$C_4$)alkoxy such as methoxy, preferably ($C_1$-$C_4$)alkyl such as methyl.
- $R^c$ represents a hydrogen atom or a ($C_1$-$C_4$)alkyl group, preferably a hydrogen atom;
- $R^f$ represents a ($C_1$-$C_4$)alkyl group such as methyl, ($C_1$-$C_4$)alkoxy such as methoxy, or —O—$(SiR_2)_x$—R' with R representing a ($C_1$-$C_4$)alkyl group such as methyl and R' a hydroxyl or ($C_1$-$C_4$)alkoxy group such as methoxy;
- $R^g$ represents a hydrogen atom or a ($C_1$-$C_6$)alkyl group,
- ALK represents a ($C_1$-$C_6$)alkylene group, preferably ethylene,
- ALK' represents a ($C_1$-$C_6$)alkylene group, preferably propylene,
- n and m, which may be identical or different, representing an integer greater than 2, x is an integer greater than or equal to 0; preferably, the values of m, n and x are such that the weight-average molecular weight of the silicone is between 2000 and 700 000, preferentially between 5000 and 500 000;

Even more particularly. (IV"e) represents:

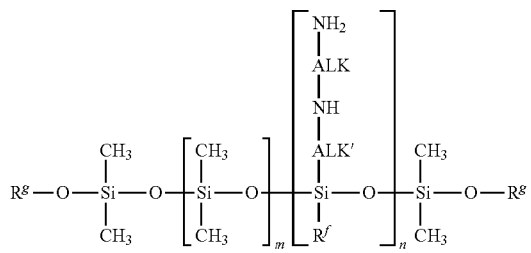

with $R^f$, $R^g$, ALK, ALK', m, n as defined for (IV"e). The amodimethicones and trimethylsiloxy amodimethicones belonging to formula (IV"e) and the formula above are, for example, the amodimethicones and trimethylsiloxy amodimethicones of ADM type sold by the company Wacker-Belsil®; mention may also be made of polydimethylsiloxanes bearing aminoethylaminopropyl groups, bearing a methoxy and/or hydroxyl function and α-ω silanols as a cationic 60% aqueous emulsion (supplier reference: Xiameter MEM-8299 Emulsion by Dow Corning or supplier reference: Belsil ADM 4000 E by Wacker);

Polydimethylsiloxane bearing an aminoethyl iminopropyl group, as a stored nonionic 15% microemulsion (supplier reference: Belsil ADM Log 1);

the polyether amines known notably under the reference Jeffamine from the company Huntsman; and notably: polyethylene glycol and/or polypropylene glycol α,ω-diamines (bearing a chain-end amine function), such as those sold under the names Jeffamine D-230, D-400, D-2000, D-4000, ED-600, ED-9000, ED-2003;

polytetrahydrofuran (or polytetramethylene glycol) α,ω-diamines, polybutadiene α,ω-diamines;

polyamidoamine (PANAM) dendrimers with amine end functions;

poly(meth)acrylates or poly(meth)acrylamides bearing primary or secondary amine side functions, such as poly(3-aminopropyl)methacrylamide or poly(2-aminoethyl) methacrylate.

As polyamine compounds bearing several amino polymer primary amine and/or secondary amine groups e), use is preferably made of polydi($C_1$-$C_4$)alkylsiloxanes comprising primary amine groups at the chain end or on side chains.

Advantageously, the polyamine compounds e) used in the process according to the invention are chosen from polydi($C_1$-$C_4$)alkylsiloxanes comprising primary amine groups at the chain end and/or on side chains.

More preferentially, the amine compound(s) iv) included in composition (B) of the process of the invention are chosen from those of formulae (IVb) and (IVe) as defined previously and even more preferentially (IV'b) and (IV'e) as defined previously.

According to a particular embodiment of the invention, composition (B) also comprises one or more hydrocarbon-based oils ill) as defined previously. Advantageously, the hydrocarbon-based oils contained in dispersion (A) and in composition (B) are identical.

According to a preferred embodiment of the invention, the hydrocarbon-based oil(s) of composition (B) are chosen from hydrocarbon-based oils containing from 8 to 14 carbon atoms, in particular the apolar oils, described previously. Even more preferentially, the hydrocarbon-based oil(s) of composition (B) are isododecane.

According to a particular embodiment of the invention, composition (B) is aqueous or aqueous-alcoholic. The term "aqueous-alcoholic" refers to a mixture of water and of a linear or branched $C_2$-$C_4$ alkanol, preferably ethanol.

According to one advantageous embodiment of the invention, composition (B) is aqueous or aqueous-alcoholic and preferably also comprises one or more chitosans and/or one or more polyamino acids, preferably polylysines.

According to another advantageous embodiment of the invention, composition (B) is aqueous and comprises one or more alkoxysilanes f) as defined previously in emulsion in water, in particular of water-in-oil (W/O) type.

According to yet another advantageous embodiment of the invention, composition (B) is aqueous and comprises one or more polyamines e) as defined previously in emulsion of oil-in-water (O/W) type.

Advantageously, the amine compound(s) used in the process according to the invention are used in a mole ratio of amine group of the amine compound iv)/ethylenically unsaturated anhydride compound anhydride b) as defined previously ranging from 0.01 to 10, preferably ranging from 0.1 to 5, preferentially ranging from 0.1 to 2 and more preferentially ranging from 0.1 to 1.

The at least two-step process of the invention makes it possible to obtain deposits of dyes and/or pigments which have good resistance to the external attacking factors to which keratin fibers may be subjected, notably good resistance to water and to successive shampoo washes.

In addition, the process of the invention makes it possible to trap nonvolatile compounds, notably oils, in order, for example, to improve the cosmeticity, or to give keratin fibers sheen, and to do so in a manner that is persistent with respect to the external attacking factors to which keratin fibers may be subjected, notably successive shampoo washes.

Nonvolatile oils that may be mentioned include: hydrocarbon-based oils of animal origin such as perhydrosqualene; hydrocarbon-based plant oils such as liquid triglycerides of fatty acids of 4 to 10 carbon atoms, such as heptanoic or octanoic acid triglycerides, or alternatively sunflower oil, corn oil, soybean oil, grapeseed oil, sesame oil, apricot oil, macadamia oil, castor oil, avocado oil, caprylic/capric acid triglycerides, jojoba oil, shea butter oil; linear or branched hydrocarbons, of mineral or synthetic origin such as liquid paraffins and derivatives thereof, petroleum jelly, polydecenes, hydrogenated polyisobutene such as Parleam; synthetic esters and ethers, notably of fatty acids, for instance purcellin oil, isopropyl myristate, 2-ethylhexyl palmitate, 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate, triisocetyl citrate, fatty alkyl heptanoates, octanoates or decanoates; polyol esters, for instance propylene glycol dioctanoate, neopentyl glycol diheptanoate, diethylene glycol diisononanoate; and pentaerythritol esters; fatty alcohols containing from 12 to 26 carbon atoms, for instance octyldodecanol, 2-butyloctanol, 2-hexyldecanol, 2-undecylpentadecanol, oleyl alcohol; partially hydrocarbon-based and/or silicone-based fluoro oils; silicone oils, for instance volatile or nonvolatile, linear or cyclic polymethylsiloxanes (PDMSs), which are liquid or pasty at room temperature, for instance cyclomethicones or dimethicones, optionally including a phenyl group, for instance phenyl trimethicones, phenyltrimethyldiphenylsiloxanes, diphenylmethyldimethyltrisiloxanes, diphenyl dimethicones, phenyl dimethicones, polymethylphenylsiloxanes; mixtures thereof.

These oils may be present in a content ranging from 0.01% to 60% by weight and better still from 0.1% to 50% by weight relative to the total weight of dispersion (A).

The Oily Dispersion (D)

The oily dispersion (D) according to the invention comprises the ingredients i), ii), iii) and iv) as described above. Preferably, the oily dispersion (D) is obtained by mixing dispersion (A) and composition (B) before applying to the keratin fibers.

The ingredients i), ii) and iii) may be included in the oily dispersion (D) in contents identical to those described above for dispersion (A).

The ingredient iv) may be included in the oily dispersion (D) in a content identical to that described above for composition (B).

Dispersions (A) and (D) and compositions (B) and (C) according to the invention may also comprise one or more dyestuffs chosen from liposoluble dyes and pulverulent dyestuffs, for instance pigments, nacres and glitter flakes that are well known to those skilled in the art. The dyestuffs may be present in the composition in a content ranging from 0% to 30% by weight, relative to the weight of the dispersion or composition which comprises them, preferably from 0% to 10% by weight.

Dispersions (A) and (D) and compositions (B) and (C) according to the invention may also comprise one or more fillers, notably in a content ranging from 0.01% to 30% by weight, relative to the weight of the dispersion or composition which comprises them.

v) The Dye(s) and Pigment(s)

According to a particular embodiment of the invention, dispersion (A) or (D) and/or composition (B) and/or composition (C) of the invention comprise v) one or more hair dyes and/or pigments.

According to a particular embodiment of the invention, dispersion (A) comprises v) one or more hair dyes.

According to another particular embodiment of the invention, dispersion (D) comprises v) one or more hair dyes.

According to yet another particular embodiment of the invention, composition (B) comprises v) one or more hair dyes.

According to a preferred embodiment of the invention, composition (C) comprises v) one or more hair dyes.

The term "hair dyes" refers to oxidation dyes, direct dyes used for dyeing keratin fibers, notably human keratin fibers such as the hair.

Among the hair dyes that may be mentioned are:
oxidation dyes, which are generally chosen from one or more oxidation bases, optionally combined with one or more coupling agents.

By way of example, the oxidation bases are chosen from para-phenylenediamines, and bis(phenyl)alkylenediamines, para-aminophenols, ortho-aminophenols heterocyclic bases and the corresponding addition salts, optionally combined with coupling agents, in particular chosen from meta-phenylenediamines, meta-aminophenols, meta-diphenols, naphthalene-based coupling agents and heterocyclic coupling agents and also the corresponding addition salts;

direct dyes, notably azo direct dyes; (poly)methine dyes such as cyanines, hemicyanines and styryls; carbonyl dyes; azine dyes; nitro(hetero)aryl dyes; tri(hetero)arylmethane dyes; porphyrin dyes; phthalocyanine dyes and natural direct dyes, alone or in the form of mixtures. The direct dyes may be anionic, cationic or neutral.

natural dyes, notably chosen from hennotannic acid, juglone, alizarin, purpurin, carminic acid, kermesic acid, purpurogallin, protocatechaldehyde, indigo, isatin, curcumin, spinulosin, apigenidin and orcein, and also extracts or decoctions containing these natural dyes.

The hair dye(s) more particularly represent from 0.001% to 10% by weight and preferably from 0.005% to 5% by weight of the total weight of the composition which comprises them.

According to a particular embodiment of the invention, dispersion (A) comprises v) one or more pigments.

According to another particular embodiment of the invention, dispersion (D) comprises v) one or more pigments.

According to another particular embodiment of the invention, composition (B) comprises v) one or more pigments.

According to another preferred embodiment of the invention, composition (C) comprises v) one or more pigments.

The term "pigment" refers to any pigment that gives color to keratin fibers. The solubility of the pigments in water at 25° C. and at atmospheric pressure (760 mmHg) is less than 0.05% by weight, and preferably less than 0.01%.

They are white or colored solid particles which are naturally insoluble in the hydrophilic and lipophilic liquid phases usually employed in cosmetics or which are rendered insoluble by formulation in the form of a lake, where appropriate. More particularly, they are pigments with little or no solubility in aqueous-alcoholic media.

The pigments that may be used are notably chosen from the organic and/or mineral pigments known in the art, notably those described in Kirk-Othmer's *Encyclopedia of Chemical Technology* and in Ullmann's *Encyclopedia of Industrial Chemistry*. Pigments that may notably be mentioned include organic and inorganic pigments such as those defined and described in Ullmann's *Encyclopedia of Industrial Chemistry* "Pigment organics", 2005 Wiley-VCH Verlag Gmbh & Co. KGaA, Weinheim 10.1002/14356007.a20 371 and ibid, "Pigments, Inorganic, 1. General" 2009 Wiley-VCH Verlag Gmbh & Co. KGaA, Weinheim 10.1002/14356007.a20_243.pub3

These pigments may be in pigment powder or paste form. They may be coated or uncoated.

The pigments may be chosen, for example, from mineral pigments, organic pigments, lakes, pigments with special effects such as nacres or glitter flakes, and mixtures thereof.

The pigment may be a mineral pigment. The term "mineral pigment" refers to any pigment that satisfies the definition in Ullmann's encyclopedia in the chapter on inorganic pigments.

Among the mineral pigments that are useful in the present invention, mention may be made of iron oxides, chromium oxides, manganese violet, ultramarine blue, chromium hydrate, ferric blue and titanium oxide.

The pigment may be an organic pigment. The term "organic pigment" refers to any pigment that satisfies the definition in Ullmann's encyclopedia in the chapter on organic pigments.

The organic pigment may notably be chosen from nitroso, nitro, azo, xanthene, quinoline, anthraquinone, phthalocyanine, metal complex type, isoindolinone, isoindoline, quinacridone, perinone, perylene, diketopyrrolopyrrole, thioindigo, dioxazine, triphenylmethane and quinophthalone compounds.

In particular, the white or colored organic pigments may be chosen from carmine, carbon black, aniline black, azo yellow, quinacridone, phthalocyanin blue, sorghum red, the blue pigments codified in the Color Index under the references CI 42090, 69800, 69825, 73000, 74100, 74160, the yellow pigments codified in the Color Index under the references CI 11680, 11710, 15985, 19140, 20040, 21100, 21108, 47000, 47005, the green pigments codified in the Color Index under the references CI 61565, 61570, 74260, the orange pigments codified in the Color Index under the references CI 11725, 15510, 45370, 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, 75470, the pigments obtained by oxidative polymerization of indole or phenolic derivatives as described in patent FR 2 679 771.

According to a particular embodiment of the invention, the pigment(s) used are pigment pastes of organic pigments such as the products sold by the company Hoechst under the name:
Cosmenyl Yellow IOG: Yellow 3 pigment (CI 11710);
Cosmenyl Yellow G: Yellow 1 pigment (CI 11680);
Cosmenyl Orange GR: Orange 43 pigment (CI 71105);
Cosmenyl Red R: Red 4 pigment (CI 12085);
Carmine Cosmenyl FB: Red 5 pigment (CI 12490);

Cosmenyl Violet RL: Violet 23 pigment (CI 51319);
Cosmenyl Blue A2R: Blue 15.1 pigment (CI 74160);
Cosmenyl Green GG: Green 7 pigment (CI 74260);
Cosmenyl Black R: Black 7 pigment (CI 77266).

The pigments in accordance with the invention may also be in the form of composite pigments, as described in patent EP 1 184 426. These composite pigments may be composed notably of particles including:
- an inorganic core,
- at least one binder for fixing the organic pigments to the core, and
- at least one organic pigment at least partially covering the core.

The term "lake" refers to dyes adsorbed onto insoluble particles, the assembly thus obtained remaining insoluble during use. The mineral substrates onto which the dyes are adsorbed are, for example, alumina, silica, calcium sodium borosilicate or calcium aluminum borosilicate and aluminum. Among the organic dyes, mention may be made of cochineal carmine.

Examples of lakes that may be mentioned include the products known under the following names: D & C Red 21 (CI 45 380), D & C Orange 5 (CI 45 370), D & C Red 27 (CI 45 410), D & C Orange 10 (CI 45 425), D & C Red 3 (CI 45 430), D & C Red 7 (CI 15 850:1), D & C Red 4 (CI 15 510), D & C Red 33 (CI 17 200), D & C Yellow 5 (CI 19 140), D & C Yellow 6 (CI 15 985), D & C Green (CI 61 570), D & C Yellow 1 O (CI 77 002), D & C Green 3 (CI 42 053) or D & C Blue 1 (CI 42 090).

The mineral substrates onto which the dyes are adsorbed are, for example, alumina, silica, calcium sodium borosilicate or calcium aluminum borosilicate and aluminum.

Among the dyes, mention may be made of cochineal carmine. Mention may also be made of the dyes known under the following names: D&C Red 21 (CI 45 380), D&C Orange 5 (C) 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), D&C Blue 1 (CI 42 090).

An example of a lake that may be mentioned is the product known under the following name: D&C Red 7 (CI 15 850:1).

The pigment(s) may also be pigments with special effects.

The term "pigments with special effects" refers to pigments that generally create a colored appearance (characterized by a certain shade, a certain vivacity and a certain level of luminance) that is nonuniform and that changes as a function of the conditions of observation (light, temperature, angles of observation, etc.). They thus contrast with colored pigments that afford a standard uniform opaque, semi-transparent or transparent shade. Several types of pigments with special effects exist: those with a low refractive index, such as fluorescent, photochromic or thermochromic pigments, and those with a higher refractive index, such as nacres or glitter flakes.

Examples of pigments with special effects that may be mentioned include nacreous pigments such as titanium mica coated with an iron oxide, mica coated with an iron oxide, mica coated with bismuth oxychloride, titanium mica coated with chromium oxide, titanium mica coated with an organic dye notably of the abovementioned type, and also nacreous pigments based on bismuth oxychloride. They may also be mica particles, at the surface of which are superposed at least two successive layers of metal oxides and/or of organic dyestuffs.

The nacres may more particularly have a yellow, pink, red, bronze, orange, brown, gold and/or coppery color or tint.

As illustrations of nacres that may be used in the context of the present invention, mention may notably be made of the gold-colored nacres sold notably by the company Engelhard under the name Gold 222C (Cloisonne), Sparkle gold (Timica), Gold 4504 (Chromalite) and Monarch gold 233X (Cloisonne); the bronze nacres sold notably by the company Merck under the names Bronze fine (17384) (Colorona) and Bronze (17353) (Colorona), by the company Eckart under the name Prestige Bronze and by the company Engelhard under the name Super bronze (Cloisonne); the orange nacres sold notably by the company Engelhard under the names Orange 363C (Cloisonne) and Orange MCR 101 (Cosmica) and by the company Merck under the names Passion orange (Colorona) and Matte orange (17449) (Microna); the brown-tinted nacres sold notably by the company Engelhard under the names Nu-antique copper 340XB (Cloisonne) and Brown CL4509 (Chromalite): the nacres with a copper tint sold notably by the company Engelhard under the name Copper 340A (Timica) and by the company Eckart under the name Prestige Copper; the nacres with a red tint sold notably by the company Merck under the name Sienna fine (17386) (Colorona); the nacres with a yellow tint sold notably by the company Engelhard under the name Yellow (4502) (Chromalite): the red-tinted nacres with a golden tint sold notably by the company Engelhard under the name Sunstone G012 (Gemtone); the black nacres with a golden tint sold notably by the company Engelhard under the name Nu-antique bronze 240 AB (Timica); the blue nacres sold notably by the company Merck under the names Matte blue (17433) (Microna), Dark Blue (117324) (Colorona); the white nacres with a silvery tint sold notably by the company Merck under the name Xirona Silver; and the golden-green pinkish-orange nacres sold notably by the company Merck under the name Indian summer (Xirona), and mixtures thereof.

In addition to nacres on a mica support, multilayer pigments based on synthetic substrates such as alumina, silica, sodium calcium borosilicate or calcium aluminum borosilicate, and aluminum, may be envisaged.

Mention may also be made of pigments with an interference effect which are not attached to a substrate, such as liquid crystals (Helicones HC from Wacker) or interference holographic glitter flakes (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

The variety of pigments that may be used in the present invention makes it possible to obtain a wide range of colors, and also particular optical effects such as metallic effects or interference effects.

The size of the pigment used in the cosmetic composition according to the present invention is generally between 10 nm and 200 µm, preferably between 20 nm and 80 µm and more preferably between 30 nm and 50 µm.

The pigments may be dispersed in the product by means of a dispersant.

The term "dispersant" refers to a compound which can protect the dispersed particles from agglomerating or flocculating. This dispersant may be a surfactant, an oligomer, a polymer or a mixture of several thereof, bearing one or more functionalities with strong affinity for the surface of the particles to be dispersed. In particular, they may become physically or chemically attached to the surface of the pigments. These dispersants also contain at least one functional group that is compatible with or soluble in the continuous medium. Said agent may be charged: it may be anionic, cationic, zwitterionic or neutral.

According to a particular embodiment of the invention, the dispersants used are chosen from 12-hydroxystearic acid esters, more particularly, and from $C_8$ to $C_{20}$ fatty acid esters of polyols such as glycerol or diglycerol, such as poly(12-hydroxystearic acid) stearate with a molecular weight of approximately 750 g/mol, such as the product sold under the name Solsperse 21 000 by the company Avecia, polyglyceryl-2 dipolyhydroxystearate (CTFA name) sold under the reference Dehymyls PGPH by the company Henkel, or polyhydroxystearic acid such as the product sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments used in the cosmetic composition according to the invention may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described notably in Cosmetics and Toiletries, February 1990, Vol. 105, pages 53-64, before being dispersed in the composition in accordance with the invention. These organic agents may be chosen, for example, from amino acids; waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminum salts of fatty acids, for example aluminum stearate or laurate; metal alkoxides; polysaccharides, for example chitosan, cellulose and derivatives thereof; polyethylene; (meth)acrylic polymers, for example polymethyl methacrylates; polymers and copolymers containing acrylate units; proteins; alkanolamines; silicone compounds, for example silicones, polydimethylsiloxanes, alkoxysilanes, alkylsilanes and siloxysilicates; organofluorine compounds, for example perfluoroalkyl ethers; fluorosilicone compounds.

The surface-treated pigments that are useful in the cosmetic composition according to the invention may also have been treated with a mixture of these compounds and/or may have undergone several surface treatments.

The surface-treated pigments that are useful in the context of the present invention may be prepared according to surface-treatment techniques that are well known to those skilled in the art, or may be commercially available as is.

Preferably, the surface-treated pigments are coated with an organic layer.

The organic agent with which the pigments are treated may be deposited on the pigments by solvent evaporation, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is notably described in patent U.S. Pat. No. 4,578,266.

An organic agent covalently bonded to the pigments will preferably be used.

The agent for the surface treatment may represent from 0.1% to 50% by weight, preferably from 0.5% to 30% by weight and even more preferentially from 1% to 10% by weight relative to the total weight of the surface-treated pigments.

Preferably, the surface treatments of the pigments are chosen from the following treatments:
 a PEG-silicone treatment, for instance the AQ surface treatment sold by LCW;
 a chitosan treatment, for instance the CTS surface treatment sold by LCW;
 a triethoxycaprylylsilane treatment, for instance the AS surface treatment sold by LCW;
 a methicone treatment, for instance the SI surface treatment sold by LOW;
 a dimethicone treatment, for instance the Covasil 3.05 surface treatment sold by LCW;
 a dimethicone/trimethyl siloxysilicate treatment, for instance the Covasil 4.05 surface treatment sold by LCW;
 a lauroyllysine treatment, for instance the LL surface treatment sold by LCW;
 a lauroyllysine dimethicone treatment, for instance the LL/SI surface treatment sold by LCW;
 a magnesium myristate treatment, for instance the MM surface treatment sold by LCW;
 an aluminum dimyristate treatment, such as the MI surface treatment sold by Miyoshi;
 a perfluoropolymethylisopropyl ether treatment, for instance the FHC surface treatment sold by LCW;
 an isostearyl sebacate treatment, for instance the HS surface treatment sold by Miyoshi;
 a disodium stearoyl glutamate treatment, for instance the NAI surface treatment sold by Miyoshi;
 a dimethicone/disodium stearoyl glutamate treatment, for instance the SA/NAI surface treatment sold by Miyoshi;
 a perfluoroalkyl phosphate treatment, for instance the PF surface treatment sold by Daito;
 an acrylate/dimethicone copolymer and perfluoroalkyl phosphate treatment, for instance the FSA surface treatment sold by Daito;
 a polymethylhydrosiloxane/perfluoroalkyl phosphate treatment, for instance the FS01 surface treatment sold by Daito;
 a lauryllysine/aluminum tristearate treatment, for instance the LL-StAl surface treatment sold by Daito;
 an octyltriethylsilane treatment, for instance the OTS surface treatment sold by Daito;
 an octyltriethylsilane/perfluoroalkyl phosphate treatment, for instance the FOTS surface treatment sold by Daito;
 an acrylate/dimethicone copolymer treatment, for instance the ASC surface treatment sold by Daito;
 an isopropyl titanium triisostearate treatment, for instance the ITT surface treatment sold by Daito;
 a microcrystalline cellulose and carboxymethylcellulose treatment, for instance the AC surface treatment sold by Daito;

a cellulose treatment, for instance the C2 surface treatment sold by Daito;

an acrylate copolymer treatment, for instance the APD surface treatment sold by Daito;

a perfluoroalkyl phosphate/isopropyl titanium triisostearate treatment, for instance the PF+ITT surface treatment sold by Daito.

The composition in accordance with the present invention may furthermore comprise one or more surface-untreated pigments.

According to one particular embodiment of the invention, the pigment(s) are mineral pigments.

According to another particular embodiment of the invention, the pigment(s) are chosen from nacres.

According to a particular embodiment of the invention, the dispersant is present with organic pigments in dispersion (A) or (D), composition (B) or (C) or with inorganic pigments in particulate form of submicron size.

The term "submicron" or "submicronic" refers to pigments having a particle size that has been micronized by a micronization method and having a mean particle size of less than a micrometer (μm), in particular between 0.1 and 0.9 μm, and preferably between 0.2 and 0.6 μm.

According to one embodiment, the dispersant and the pigment(s) are present in an amount (dispersant:pigment) of between 0.5:1 and 2:1, particularly between 0.75:1 and 1.5:1 or better still between 0.8:1 and 1.2:1.

According to a particular embodiment, the dispersant is suitable for dispersing the pigments and is compatible with a condensation-curable formulation.

The term "compatible" means, for example, that said dispersant is miscible in the oily phase of the composition or of the dispersion containing the pigment(s), and it does not retard or reduce the curing. The dispersant is preferably cationic.

The dispersant(s) may therefore have a silicone backbone, such as silicone polyether and dispersants of aminosilicone type. Among the suitable dispersants that may be mentioned are:

aminosilicones, i.e. silicones comprising one or more amino groups such as those sold under the names and references: BYK LPX 21879 by BYK, GP-4, GP-6, GP-344, GP-851, GP-965, GP-967 and GP-988-1, sold by Genesee Polymers, silicone acrylates such as Tego® RC 902, Tego® RC 922, Tego® RC 1041, and Tego RC 1043, sold by Evonik, polydimethylsiloxane (PDMS) silicones bearing carboxylic groups, such as X-22162 and X-22370 sold by Shin-Etsu, epoxy silicones such as GP-29, GP-32, GP-502, GP-504, GP-514, GP-607, GP-682, and GP-695 sold by Genesee Polymers, or Tego® RC 1401, Tego® RC 1403, Tego® RC 1412 sold by Evonik.

According to a particular embodiment, the dispersant(s) are of aminosilicone type and are positively charged.

Mention may also be made of dispersants bearing chemical groups that are capable of reacting with the reagents of the oily phase and are thus capable of improving the 3D network formed from the aminosilicones. For example, dispersants of epoxy silicone pigments can react chemically with the aminosilicone prepolymer amino group(s) to increase the cohesion of the aminosilicone film comprising the pigment(s).

Preferably, the pigment(s) v) of the invention are chosen from carbon black, iron oxides, notably brown or black iron oxides, and micas coated with iron oxide, triarylmethane pigments, notably blue and purple triarylmethane pigments, such as Blue 1 Lake, azo pigments, notably red azo pigments, such as D&C Red 7, an alkali-earth metal salt of lithol red, such as the calcium salt of lithol red B.

According to a particular embodiment of the invention, the amount of pigments ranges from 0.5% to 40% and preferably from 1% to 20% relative to the weight of the composition and dispersion comprising them.

Two-Step Application Process:

According to an advantageous variant of the invention, the process of the invention is a process for treating keratin fibers, in particular human keratin fibers, preferably the hair, comprising:

1) the application to said fibers of an oily dispersion (A) comprising:

i) one or more particles constituted of one or more ethylenic copolymers a) and b) as defined previously; and ii) one or more stabilizers constituted of ethylenic polymers chosen from c) and d) as defined previously;

iii) one or more hydrocarbon-based oils as defined previously and v) one or more dyes and/or pigments; followed by 2) the application to said fibers of a composition (B) comprising:

iv) one or more amine compounds chosen from e) and f) as defined previously.

According to another advantageous variant of the invention, the process of the invention is a process for treating keratin fibers, in particular human keratin fibers, preferably the hair, comprising:

1) the application to said fibers of an oily dispersion (A) comprising:

i) one or more particles constituted of one or more ethylenic copolymers a) and b) as defined previously; and ii) one or more stabilizers constituted of ethylenic polymers chosen from c) and d) as defined previously; and iii) one or more hydrocarbon-based oils as defined previously; followed by 2) the application to said fibers of a composition (B) comprising:

iv) one or more amine compounds chosen from e) and f) as defined previously; and v) one or more dyes and/or pigments.

According to yet another variant of the invention, the process of the invention is a process for treating keratin fibers, in particular human keratin fibers, preferably the hair, comprising:

1) the application to said fibers of an oily dispersion (A) comprising:

i) one or more particles constituted of one or more ethylenic copolymers a) and b) as defined previously; and ii) one or more stabilizers constituted of ethylenic polymers chosen from c) and d) as defined previously; and iii) one or more hydrocarbon-based oils as defined previously:

followed by 2) the application to said fibers of a composition (B) comprising:

iv) one or more amine compounds chosen from e) and f) as defined previously;
followed by
3) the application to said fibers of a composition (C) comprising:
v) one or more dyes and/or pigments.

According to yet another advantageous variant of the invention, the process of the invention is a process for treating keratin fibers, in particular human keratin fibers, preferably the hair, comprising:
1) the application to said fibers of an oily dispersion (A) comprising:
i) one or more particles constituted of one or more ethylenic copolymers a) and b) as defined previously; and
ii) one or more stabilizers constituted of ethylenic polymers chosen from c) and d) as defined previously; and
iii) one or more hydrocarbon-based oils as defined previously;
followed by
2) the application to said fibers of a composition (C) comprising v) one or more dyes and/or pigments;
followed by
3) the application to said fibers of a composition (B) comprising iv) one or more amine compounds chosen from e) and f) as defined previously.

According to a particularly preferred variant of the invention, the process of the invention is a process for treating keratin fibers, in particular human keratin fibers, preferably the hair, comprising:
1) the application to said fibers of a composition (C) comprising v) one or more dyes and/or pigments;
followed by
2) the application to said fibers of an oily dispersion (A) comprising:
i) one or more particles constituted of one or more ethylenic copolymers a) and b) as defined previously; and
ii) one or more stabilizers constituted of ethylenic polymers chosen from c) and d) as defined previously; and
ili) one or more hydrocarbon-based oils as defined previously;
followed by
3) the application to said fibers of a composition (B) comprising iv) one or more amine compounds chosen from e) and f) as defined previously.

According to another variant of the invention, the process of the invention is a process for treating keratin fibers, in particular human keratin fibers, preferably the hair, comprising:
1) the application to said fibers of a composition (C) comprising v) one or more dyes and/or pigments;
followed by
2) the application to said fibers of an oily dispersion (D) comprising:
i) one or more particles constituted of one or more ethylenic copolymers a) and b) as defined previously; and
ii) one or more stabilizers constituted of ethylenic polymers chosen from c) and d) as defined previously; and
iii) one or more hydrocarbon-based oils as defined previously; and
iv) one or more amine compounds chosen from e) and f) as defined previously.

According to another particular variant of the invention, the hair dye(s) iv) as defined previously are in a composition (C). Said composition may be applied simultaneously with composition (A), or with composition (B). Preferably, composition (C) is applied after step 1a), i.e. after the application of composition (A); more preferentially, compositions (A) and (B) do not comprise any hair dye and a composition (C) comprising one or more hair dyes v) as defined previously is applied after step 1a) of the process of the invention, followed by the application to the keratin fibers of composition (B).

Dispersions (A) and (D) and compositions (B) and (C) are cosmetic, i.e. they comprise only cosmetically acceptable ingredients.

According to a particular embodiment of the invention, dispersions (A) or (D) and compositions (B) and (C) are anhydrous.

According to another advantageous embodiment, dispersions (A) or (D) and composition (B) are anhydrous, and composition (C) is aqueous.

According to a particular embodiment of the invention, composition (B) is aqueous or aqueous-alcoholic.

According to another particularly advantageous embodiment of the invention, composition (C) is aqueous or aqueous-alcoholic.

According to yet another advantageous embodiment, dispersions (A) or (D) are anhydrous and composition (B) and composition (C) are aqueous or aqueous-alcoholic, preferably aqueous.

Compositions (B) and (C) and dispersions (A) and (D) according to the invention may comprise a cosmetic additive chosen from water, fragrances, preserving agents, fillers, UV-screening agents, oils, waxes, surfactants, moisturizers, vitamins, ceramides, antioxidants, free-radical scavengers, polymers, thickeners and dyestuffs.

Compositions (B) and (C) and dispersions (A) and (D) according to the invention may also comprise other dyestuffs, such as liposoluble dyes or water-soluble dyes. This dyestuff may be present in a content ranging from 0.01% to 30% by weight, relative to the total weight of the composition.

The liposoluble dyes are, for example, Sudan Red, D&C Red 17, D&C Green 6, *-carotene, soybean oil, Sudan Brown, D&C Yellow 11, D&C Violet 2, D&C Orange 5, quinoline yellow and annatto. The water-soluble dyes are, for example, beetroot juice or methylene blue.

According to one embodiment, dispersions (A) or (D) and compositions (B) and (C) according to the invention are anhydrous compositions.

Preferentially, the first step of the process of the invention is the application of dispersions (A) or (D) in one or more volatile apolar solvents, notably isododecane.

Dispersions (A) or (D) and compositions (B) or (C) described above may be used on wet or dry keratin fibers, and also on any type of fair or dark, natural or dyed, permanent-waved, bleached or relaxed fibers.

According to a particular embodiment of the process of the invention, the fibers are washed before applying dispersion (A) or (D).

The application to the fibers may be performed via any standard means, in particular using a comb, a fine brush, a coarse brush or with the fingers.

After the application of dispersions (A) or (D), or compositions (B) and (C), the fibers may be left to dry or may be dried, for example at a temperature of greater than or equal to 30° C.

According to a particular embodiment, this temperature is greater than 40° C. According to a particular embodiment, this temperature is greater than 45° C. and less than 220° C.

Preferably, if the fibers are dried, they are dried, in addition to a supply of heat, with a flow of air.

During drying, a mechanical action may be exerted on the locks, such as combing, brushing or running the fingers through. This operation may similarly be performed once the fibers have been dried, naturally or otherwise.

The drying step of the process of the invention may be performed with a drying device such as a hood, a hairdryer, a straightening iron, a climazone, etc.

When the drying step is performed with a hood or a hairdryer, the drying temperature is between 40 and 110° C. and preferably between 50 and 90° C.

When the drying step is performed with a straightening iron, the drying temperature is between 110 and 220° C. and preferably between 140 and 200° C.

Once the drying is complete, final rinsing or shampooing may optionally be performed.

According to one preferred embodiment of the invention, step 1a) is performed on dry keratin fibers.

According to another particular embodiment of the process of the invention, step 1a) is performed on humid or wet keratin fibers.

According to an advantageous variant of the process of the invention, between step 1a) and step 1b), there is no rinsing, and drying of the keratin fibers is performed naturally or using a drying device such as a hairdryer. Preferably, after applying dispersion (A) during step 1a), there is a waiting time of between 1 minute and 6 hours, in particular between 10 minutes and 5 hours, more particularly between 30 minutes and 4 hours, and preferably about 3 hours, before applying composition (B).

According to a particular variant of the process of the invention, between step 1a) and step 1b), rinsing with water is performed one or more times successively, optionally followed by drying naturally or using a drying device such as a hairdryer.

According to another variant, step 1b) follows step 1a) without intermediate rinsing or drying.

Preferably, after applying dispersion (A) during step 1a), there is a waiting time of between 1 minute and 6 hours, in particular between 10 minutes and 5 hours, more particularly between 30 minutes and 4 hours, and preferably about 3 hours, before applying composition (B).

If the first step is the step of applying composition (C) followed by the application of the oily dispersion (A) and then the application of composition (B) between the application of composition (C) (step 1) and the step of applying dispersion (A) (step 2), the keratin fibers are preferably dried naturally or using a drying device such as a hairdryer.

If the first step is the step of applying the oily dispersion (A) and the second step is that of applying composition (C) and the third step is that of applying composition (B) between the application of composition (C) as defined previously (step 2) and the step of applying composition (B) (step 3), the keratin fibers are preferably dried naturally or using a drying device such as a hairdryer.

If the first step is the application of the oily dispersion (A) followed by the application of composition (B) and then the application of composition (C) between the application of composition (B) (step 2) and the step of applying composition (B) (step 2), the keratin fibers are preferably dried naturally or using a drying device such as a hairdryer.

The Kit

A subject of the invention is also a kit or device with several separate compartments comprising:

in a first compartment: dispersion (A) as defined previously.

in a second separate compartment: composition (B) as defined previously, and optionally in a third compartment separate from the other two: composition (C) as defined previously.

The composition packaging assembly is, in a known manner, any packaging that is suitable for storing cosmetic compositions (notably a bottle, tube, spray bottle or aerosol bottle).

A subject of the invention is also the oily dispersion (A) as defined previously, comprising v) the dye(s) and/or pigment(s) as defined previously, it being understood that when v) represents one or more pigment(s), then the dispersion is anhydrous and does not comprise any polyamine compound bearing several primary amine and/or secondary amine groups and does not comprise any amino alkoxysilanes.

A subject of the invention is also the oily dispersion (A) which is in an inverse emulsion (W/O) as defined previously.

The invention is illustrated in greater detail in the examples that follow.

EXAMPLES

Example 1

The oily dispersions (A) are formed as a whole [particles i)+stabilizer ii)] containing:

70% by weight of ($C_1$-$C_4$)alkyl ($C_1$-$C_4$)(alkyl)acrylate a) (such as ethyl acrylate), 10% by weight of ethylenically unsaturated anhydride compound b) (such as maleic anhydride), and 20% by weight of polymers of ($C_3$-$C_{12}$)cycloalkyl ($C_1$-$C_6$)(alkyl)acrylate monomers c) (such as isobornyl acrylate).

The preparation of these oily dispersions was performed in a 1 liter pilot reactor. The synthesis is performed in two steps:

In a first step, isobornyl acrylate is polymerized in isododecane/ethyl acetate (60/40) in the presence of a small amount of ethyl acrylate and of a radical initiator (T21S). In the first step, the isobornyl acrylate/ethyl acrylate mass ratio is 92/8.

In the second step, the rest of the ethyl acrylate and the maleic anhydride are added in the presence of isododecane/ethyl acetate (60/40) and of the radical initiator Trigonox 21S (T21S).

After stripping, the polymer is at a solids content of 52% in the isododecane. The ratios employed to obtain the stabilizer and the particulate core are summarized in the table below:

| | Mass percentage Stabilizer - Particulate core | Monomer | Mass percentage in the stabilizer and the particulate core |
|---|---|---|---|
| Stabilizer ii) | 22 | Isobornyl acrylate | 92 |
| | | Ethyl acrylate | 8 |
| Particulate core i) | 78 | Ethyl acrylate | 87 |
| | | Maleic anhydride | 13 |

Amount of Reagents:
Step 1:

| Reagents: | Mass (g) |
|---|---|
| Isobornyl acrylate | 50 |
| Ethyl acrylate | 4 |
| T21S | 0.54 |
| Isododecane/EtOAc (60/40) | 96 |

Isododecane Added Between the Two Steps:

| Reagent | Mass (g) |
|---|---|
| Isododecane/EtOAc (60/40) | 80 |

Step 2:

| Reagents: | Mass (g) | Mass added to the beaker for the addition (g) |
|---|---|---|
| Ethyl acrylate | 171 | 196.65 |
| Maleic anhydride | 25 | 28.7 |
| T21S | 1.96 | 2.25 |
| Isododecane/EtOAc (60/40) | 196 | 225.4 |

Experimental Protocol:

Isododecane/ethyl acetate (60/40), isobornyl acrylate, ethyl acrylate and T21S are introduced as feedstock into a reactor. The medium is heated to 90° C. under argon and with stirring. The solids content during this first step is 35.9%.

After heating for 2 hours, NMR indicates an isobornyl acrylate consumption of 97% (ethyl acrylate consumption: 97%).

After 2 hours of reaction, isododecane/ethyl acetate (60/40) are introduced into the feedstock. The medium is heated to 90° C.

Once the medium is at 90° C., ethyl acrylate/maleic anhydride, isododecane/ethyl acetate (60/40) and T21S are introduced over 2 hours by pouring. At the end of the introduction by pouring, the medium is milky. The solids content is 40%.

After 7 hours of synthesis, traces of the starting monomers remain.

1 L of isododecane and of ethyl acetate are then stripped out (NMR indicates that there are no more monomers and that the ethyl acetate has been totally removed from the dispersion). The solids content is about 52%.

Example 2

The combination of particles i)+stabilizer ii) was prepared in the following manner;
- 75% by weight of ($C_1$-$C_4$)alkyl ($C_1$-$C_4$)(alkyl)acrylate a) (such as ethyl acrylate),
- 5% by weight of ethylenically unsaturated anhydride compound b) (such as maleic anhydride), and
- 20% by weight of polymers of ($C_3$-$C_{12}$)cycloalkyl ($C_1$-$C_6$)(alkyl)acrylate monomers c) (such as isobornyl acrylate).

The synthesis was performed in a 1 liter pilot reactor in two steps:

In a first step, isobornyl acrylate is polymerized in isododecane/ethyl acetate (60/40) in the presence of a small amount of ethyl acrylate and of a radical initiator (T21S). In the first step, the isobornyl acrylate/ethyl acrylate mass ratio is 92/8.

In the second step, the rest of the ethyl acrylate and the maleic anhydride are added in the presence of isododecane/ethyl acetate (60/40) and of the radical initiator (T21S).

After stripping, the polymer is at a solids content of 49% in the isododecane.

The ratios employed to obtain the stabilizer and the particulate core are summarized in the table below:

| | Mass percentage Stabilizer - Particulate core | Monomer | Mass percentage in the stabilizer and the particulate core |
|---|---|---|---|
| Stabilizer ii) | 22 | Isobornyl acrylate | 92 |
| | | Ethyl acrylate | 8 |
| Particulate core i) | 78 | Ethyl acrylate | 94 |
| | | Maleic anhydride | 6 |

Amount of Reagents:
Step 1:

| Reagents: | Mass (g) |
|---|---|
| Isobornyl acrylate | 50 |
| Ethyl acrylate | 4 |
| T21S | 0.52 |
| Isododecane/EtOAc (60/40) | 96 |

Isododecane Added Between the Two Steps:

| Reagent | Mass (g) |
|---|---|
| Isododecane/EtOAc (60/40) | 80 |

Step 2:

| Reagents: | Mass (g) | Mass added to the beaker for the addition (g) |
|---|---|---|
| Ethyl acrylate | 183.5 | 211.03 |
| Maleic anhydride | 12.5 | 14.38 |
| T21S | 1.96 | 2.25 |
| Isododecane/EtOAc (60/40) | 196 | 225.4 |

Experimental Protocol:

Isododecane/ethyl acetate (60/40), isobornyl acrylate, ethyl acrylate and T21S are introduced as feedstock into the reactor. The medium is heated to 90° C. (nominal medium temperature) under argon and with stirring. The solids content during this first step is 35.9%.

After heating for 2 hours, NMR indicates an isobornyl acrylate consumption of 98% (ethyl acrylate consumption: 97%).

After 2 hours of reaction, isododecane/ethyl acetate (60/40) are introduced into the feedstock. The medium is heated to 90° C.

Once the medium is at 90° C., ethyl acrylate/maleic anhydride, isododecane/ethyl acetate (60/40) and T21S are introduced over 2 hours by addition. At the end of the introduction by addition, the medium is milky. The solids content is 40%.

After 7 hours of synthesis, traces of the starting monomers remain.

1 L of isododecane and of ethyl acetate are then stripped (NMR indicates that there are no more monomers and that the ethyl acetate has been totally removed from the dispersion). The solids content is about 49%.

Amine Compounds Used:

| Amine compound 1 | Amine compound 2 |
|---|---|
| Poly(dimethylsiloxane), bis(3-aminopropyl) terminated (PDMS-diNH$_2$) (CAS Number: 106214-84-0) (Mn = 50 000 g/mol) | Bis-cetearyl amodimethicone, 2-[(2-aminoethyl)amino]propyl Me, di-Me, [(C$_{14-20}$-alkyldimethylsilyl)oxy]-terminated (CAS Number: 1126942-72-0) |

The various combinations were evaluated in terms of the "hair strand makeup" or coating of keratin fibers, i.e. the coating of the keratin fibers with dyes/pigments. A comparison of the resistance to shampoo washing of the coatings was performed with the comparative composition below.

2-Step Process:

The following compositions and dispersions were prepared. The amounts are given in g per 100 g of dispersion or composition.

Dispersion (A1):

| Ingredients | Amount (g) |
|---|---|
| Combination of particle example 1, ingredients i), ii) | 10 (active material - a.m.) |
| D&C Black 2 (carbon black) dispersed in isododecane, polyglyceryl-3 diisostearate, propylene carbonate and quaternary amine/mineral clay complex, ingredient v), | 3 |
| Isododecane, ingredient iii) | qs 100 |

Composition (B1)

| Ingredients | Amount (g) |
|---|---|
| Amine compound 2, ingredient iv) | 5 (a.m.) |
| Isododecane, ingredient iii) | 95 |

The various steps of the protocol for applying to keratin fibers (natural hair containing 90% white hairs, also known as 90% NW):

Application to the keratin fibers (dry hair) of dispersion (Ax) in a bath ratio of 0.5 g of dispersion or composition/g of hair;

The lock is dried with a hairdryer;

3 hours after application of dispersion (Ax), application of composition (Bx) in a bath ratio of 0.5 g of composition (Bx)/g of hair; and then The lock is dried with a hairdryer.

The evaluations in terms of resistance to shampoo washing are thus performed 24 hours after the application.

Example 3: Application in 2 Steps—Dispersion (A1) Comprising Example 1+Carbon Black, Followed by Application of Composition (B1) Comprising the Amine Compound 2

A test was performed by applying only dispersion (A1). The tests of resistance to shampoo washing were observed after application of dispersion (A1) alone and for the process according to the invention, i.e. after application of dispersion (A1) and of composition (B1) or (B2).

The evaluation results are summarized in the tables below:

After application of dispersion (A1) before and after two shampoo washes: It is seen visually that the black coloring obtained after application of dispersion (A1) has almost completely disappeared after two shampoo washes.

These observations were corroborated with the L*, a* and b* colorimetric measurement results.

The colorimetric data for each of the locks are measured with a Minolta CM-3610d spectrophotometer. In this L*a*b* system, L* represents the lightness, a* indicates the green/red color axis and b* indicates the blue/yellow color axis. The higher the value of L, the lighter or less intense the color. Conversely, the lower the value of L, the darker or more intense the color. The higher the value of a*, the redder the shade, and the higher the value of b*, the yellower the shade.

Colorimetric Measurements:

| Number of shampoo washes | L |
|---|---|
| 0 shampoo washes | 28.92 |
| 2 shampoo washes | 62.23 |

After application of dispersion (A1) before and after two shampoo washes: It is seen that the intense black coloring (L=28.92) obtained after application of dispersion (A1) has almost completely disappeared after two shampoo washes (L=62.23).

After application of dispersion (A1) and then of composition (B1) at 0, then 1 and then 5 shampoo washes:

Visually, the intense black coloring appears unchanged between the coloring obtained just after having performed the process of the invention and after 1 and 5 successive shampoo washes. In addition, the hair strands appear individualized after treatment, with a respected volume, and this is found even after 5 shampoo washes. The feel is very pleasant.

The colorimetric results were corroborated with the L', at and b* colorimetric measurement and color build-up results.

The color build-up on hair thus corresponds to the variation in coloring between the locks of dyed NW hair (natural gray hair containing 90% white hairs) and the non-dyed (i.e. untreated) NW hair, which is measured by (ΔE) according to the following equation:

$$\Delta E = \sqrt{(L^* - L_o^*)^2 + (a^* - a_o^*)^2 + (b^* - b_o^*)^2}$$

In this equation, L*, a* and b* represent the values measured after dyeing of the NW hair, and $L_o^*$, $a_o^*$ and $b_o^*$ represent the values measured before dyeing of the NW hair. The higher the DE value, the better the build-up of the coloring.

| Number of shampoo washes | L | a | b | ΔE color build-up |
|---|---|---|---|---|
| 0 shampoo washes | 28.92 | −0.16 | 2.73 | 32.21 |
| 1 shampoo wash | 30.03 | −0.31 | 3.17 | 31.02 |
| 5 shampoo washes | 29.82 | −0.12 | 3.08 | 31.24 |

It is seen from the above table that the values of L, a and b do not change significantly, after 1 shampoo wash and 5 shampoo washes.

Example 4: Application in 2 Steps—Dispersion (A2) Comprising Example 1+Pigment: Nacre Followed by Application of Composition (B1) Comprising Amine Compound 2

The following compositions and dispersions were prepared. The amounts are given in g per 100 g of dispersion or composition.

Dispersion A2

| Ingredients | Amount (g) |
|---|---|
| Combination of particle example 1, ingredients i), ii) | 15 (a.m.) |
| Nacre (Mica coated with brown iron oxide), CI 77491~ingredient v) | 6 |
| Isododecane, ingredient iii) | qs 100 |

Composition B2

| Ingredients | Amount (g) |
|---|---|
| Amine compound 2, ingredient iv) | 8 (a.m.) |
| Isododecane, ingredient iii) | qs 100 |

The intense chromatic coloring appears unchanged between the coloring obtained just after having performed the process of the invention, and this is found even after 20 successive shampoo washes:

| Number of shampoo washes | L | a | b | ΔE color build-up |
|---|---|---|---|---|
| 0 shampoo washes | 34.88 | −14.19 | −11.39 | 40.63 |
| 20 shampoo washes | 36.34 | −14.45 | −10.63 | 39.31 |

Example 5: Application in 2 Steps—Dispersion (A2) Comprising Example 1+Pigment: Nacre Followed by Application of Composition (B1) Comprising Amine Compound 2

Dispersion A2

| Ingredients | Amount (g) |
|---|---|
| Combination of particle example 1, ingredients i), ii) | 15 (a.m.) |
| Nacre (mica coated with brown iron oxide)-ingredient v) | 6 |
| Isododecane, ingredient iii) | qs 100 |

Composition (B1)

| Ingredients | Amount (g) |
|---|---|
| Amine compound 2, ingredient iv) | 5 (a.m.) |
| Isododecane, ingredient iii) | 95 |

Visually, the chromatic coppery coloring appears unchanged between the coloring obtained just after having performed the process of the invention and after 10 or even 20 successive shampoo washes. In addition, the hair strands appear individualized after treatment, with a respected volume, and this is found even after more than 10 shampoo washes. The feel is very pleasant. These color results were corroborated with the colorimetric measurements.

Colorimetric Measurements;

| Number of shampoo washes | L | a | b | ΔE color build-up |
|---|---|---|---|---|
| 0 shampoo washes | 35.43 | −16.78 | −10.45 | 40.73 |
| 10 shampoo washes | 34.89 | −15.9 | −11.22 | 41.20 |
| 20 shampoo washes | 35.37 | −15.95 | −12.35 | 41.68 |

It is seen from the above table that the values of L, a and b and ΔE do not change significantly, after 10 or even 20 successive shampoo washes.

Example 6: Application in 2 Steps—Dispersion (A3) Comprising Example 2+Pigment: Nacre Followed by Application of Composition (B1) Comprising Amine Compound 2

Dispersion A3

| Ingredients | Amount (g) |
|---|---|
| Combination of particle example 2, ingredients i), ii) | 15 (a.m.) |
| Red 7, isopropyl titanium triisostearate, triethoxysilylethyl polydimethylsiloxyethyl dimethicone, ingredient v) | 6 |
| Isododecane, ingredient iii) | qs 100 |

Composition (B1)

| Ingredients | Amount (g) |
|---|---|
| Amine compound 2, ingredient iv) | 5 (a.m.) |
| Isododecane, ingredient iii) | 95 |

Visually, the chromatic coppery coloring appears unchanged between the coloring obtained just after having performed the process of the invention and after 10 successive shampoo washes. In addition, the hair strands appear individualized after treatment, with a respected volume, and this is found even after 10 shampoo washes. The feel is very pleasant. The color results on keratin fibers were corroborated with the L, a, b colorimetric measurements.

| Number of shampoo washes | L | a | b |
|---|---|---|---|
| 0 shampoo washes | 42.79 | 27.4 | 4.97 |
| 10 shampoo washes | 44.62 | 28.62 | 4.68 |

It is seen from the above table that the values of L, a and b do not change significantly, after 10 successive shampoo washes.

Example 7: Application in 2 Steps—Dispersion (A4) Comprising Example 1+Pigment: Black Iron Oxide Followed by Application of Composition (B1) Comprising Amine Compound 2

Dispersion (A4)

| Ingredients | Amount (g) |
|---|---|
| Combination of particle example 1, ingredients i), ii) | 15 (a.m.) |
| Black iron oxide (CI: 77499), ingredient v) | 6 |
| Isododecane, ingredient iii) | qs 100 |

Composition (B1)

| Ingredients | Amount (g) |
|---|---|
| Amine compound 2, ingredient iv) | 5 (a.m.) |
| Isododecane, ingredient iii) | 95 |

Visually, the intense and deep black coloring appears unchanged between the coloring obtained just after having performed the process of the invention and after 10 successive shampoo washes. In addition, the hair strands appear individualized after treatment, with a respected volume, and this is found even after 10 shampoo washes. The feel is very pleasant.

Example 8: Application in 2 Steps—Dispersion (A5) Comprising Example 1+Pigment: Lake Blue 1 Followed by Application of Composition (B1) Comprising Amine Compound 2

Dispersion (A5)

| Ingredients | Amount (g) |
|---|---|
| Combination of particle example 1, ingredients i), ii) | 15 (a.m.) |
| Blue 1 lake CI 42090 (&) triethoxycaprylylsilane, ingredient v) | 6 |
| Isododecane, ingredient iii) | qs 100 |

Composition (B1)

| Ingredients | Amount (g) |
|---|---|
| Amine compound 2, ingredient iv) | 8 (a.m.) |
| Isododecane, ingredient iii) | 95 |

Visually, the intense and chromatic blue coloring appears unchanged between the coloring obtained just after having performed the process of the invention and after 10 successive shampoo washes. In addition, the hair strands appear individualized after treatment, with a respected volume, and this is found even after 10 shampoo washes. The feel is very pleasant.

Example 9: Application in 2 Steps—Dispersion (A6) Comprising Example 1+Pigment: Red 7 Followed by Application of Composition (B1) Comprising Amine Compound 2

Dispersion A9

| Ingredients | Amount (g) |
|---|---|
| Combination of particle example 1, ingredients i), ii) | 15 (a.m.) |
| D&C Red 7 calcium salt of lithol red B, CI 15850, ingredient v) | 6 |
| Isododecane, ingredient iii) | qs 100 |

Composition (B1)

| Ingredients | Amount (g) |
|---|---|
| Amine compound 2, ingredient iv) | 5 (a.m.) |
| Isododecane, ingredient iii) | 95 |

Visually, the intense and chromatic red coloring appears unchanged between the coloring obtained just after having performed the process of the invention and after 10 successive shampoo washes. In addition, the hair strands appear individualized after treatment, with a respected volume, and this is found even after 10 shampoo washes. The feel is very pleasant.

Example 10: Application in 3 Steps—Composition (C1) Comprising the Pigment Black 2, Followed by Application of Dispersion (A7) Comprising Example 1, and then Application of Composition (B1) Comprising the Amine Compound 2

Application Protocol: 3-Step Protocol

The various steps of the protocol for application to 90% NW hair:

1. Application to dry hair of the pigment alone conveyed in a cosmetic solvent (water, isododecane), application of composition (C)
2. The lock is dried with a hairdryer
3. Dispersion (A7) is applied directly after drying, in a bath ratio of 0.5 g of formula/g of hair
4. The lock is dried with a hairdryer
5. 3 hours after application of (A7), application of composition (B1), in a bath ratio of 0.5 g of formula/g of hair
6. The lock is dried with a hairdryer
7. The evaluations in terms of resistance to shampoo washing are thus performed 24 hours after the application of (B1).

Composition (C)

| Ingredients | Amount (g) |
|---|---|
| D&C Black 2 (carbon black - CI 77266) & Laureth-21, ingredient v) | 3 (a.m.) |
| Water | qs 100 |

Dispersion (A7)

| Ingredients | Amount (g) |
| --- | --- |
| Combination of particle example 1, ingredients i), ii) | 10 (a.m.) |
| Isododecane, ingredient iii) | qs 100 |

Composition (B1)

| Ingredients | Amount (g) |
| --- | --- |
| Amine compound 2, ingredient iv) | 5 (a.m.) |
| Isododecane, ingredient iii) | 95 |

Visually, the intense and deep black coloring appears unchanged between the coloring obtained just after having performed the process of the invention and after 1 and 5 successive shampoo washes. In addition, the hair strands appear individualized after treatment, with a respected volume, and this is found even after 10 shampoo washes. The feel is very pleasant. The color results on keratin fibers are corroborated with the L, a, b colorimetric measurements.

Colorimetric Measurements:

| Number of shampoo washes | L | a | b | ΔE color build-up |
| --- | --- | --- | --- | --- |
| 5 shampoo washes | 25.42 | 0.1 | 2.32 | 4.9 |
| 10 shampoo washes | 25.53 | 0.05 | 1.32 | 4.6 |

It is seen from the above table that the values of L, a and b and ΔE do not change significantly, after 5 or even 10 successive shampoo washes.

Examples 11 to 13

In examples 11 to 13 below, the following dispersions and compositions were prepared. The amounts are given in g per 100 g of dispersion or composition.

The various steps of the protocol for applying to keratin fibers (natural hair containing 90% white hairs, also known as 90% NW):
 Application to the keratin fibers (dry hair) of composition (Cx), in a bath ratio of 0.5 g of dispersion or composition/g of hair;
 The lock is dried with a hairdryer;
 1 hour after application of dispersion (Cx), application of composition (D), in a bath ratio of 0.5 g of composition (D)/g of hair; and then
 The lock is dried with a hairdryer.
The evaluations in terms of resistance to shampoo washing are thus performed 24 hours after the application.

Example 11

Composition (C1)

| Ingredients | Amount (g) |
| --- | --- |
| Red iron oxide (CI: 77491), ingredient v) | 6 (a.m.) |
| Isododecane | qs 100 |

Dispersion D

| Ingredients | Amount (g) |
| --- | --- |
| Combination of particle example 1, ingredients i), ii) | 6 (a.m.) |
| Amine compound 2, ingredient iv) | 14 |
| Isododecane, ingredient iii) | qs 100 |

The colorimetric data for each of the locks are then measured with a Minolta CM-3610d spectrophotometer.

Colorimetric Measurements:

| Number of shampoo washes | L | a | b | ΔE color build-up |
| --- | --- | --- | --- | --- |
| 0 shampoo washes | 40.09 | 24.39 | 20.2 | 32.78 |
| 5 shampoo washes | 46.34 | 18.05 | 19.21 | 23.84 |

Visually, the intense red coloring appears unchanged between the coloring obtained just after having performed the process of the invention and after 5 successive shampoo washes. In addition, the hair strands appear individualized after treatment, with a respected volume, and this is found even after 5 shampoo washes. The feel is very pleasant.

Example 12

Composition (C2)

| Ingredients | Amount (g) |
| --- | --- |
| Red iron oxide treated with 2% of isopropyl titanium triisostearate, ingredient v) | 6 (a.m.) |
| Isododecane | qs 100 |

Dispersion D

| Ingredients | Amount (g) |
| --- | --- |
| Combination of particle example 1, ingredients i), ii) | 6 (a.m.) |
| Amine compound 2, ingredient iv) | 14 |
| Isododecane, ingredient iii) | qs 100 |

The colorimetric data for each of the locks are then measured with a Minolta CM-3610d spectrophotometer.

Colorimetric Measurements:

| Number of shampoo washes | L | a | b | ΔE color build-up |
| --- | --- | --- | --- | --- |
| 0 shampoo washes | 38.9 | 23.73 | 20.39 | 33.23 |
| 5 shampoo washes | 49.57 | 17.6 | 19.23 | 21.26 |

Visually, the intense red coloring appears unchanged between the coloring obtained just after having performed the process of the invention and after 1 and 5 successive shampoo washes. In addition, the hair strands appear individualized after treatment, with a respected volume, and this is found even after 5 shampoo washes. The feel is very pleasant.

Example 13

Composition (C2)

| Ingredients | Amount (g) |
| --- | --- |
| Red iron oxide 8% treated with isopropyl titanium triisostearate and triethoxysilylethyl polydimethylsiloxyethyl dimethicone, ingredient v) | 6 (a.m.) |
| Isododecane | qs 100 |

Dispersion D

| Ingredients | Amount (g) |
| --- | --- |
| Combination of particle example 1, ingredients i), ii) | 6 (a.m.) |
| Amine compound 2, ingredient iv) | 14 |
| Isododecane, ingredient iii) | qs 100 |

The colorimetric data for each of the locks are then measured with a Minolta CM-3610d spectrophotometer.
Colorimetric Measurements:

| Number of shampoo washes | L | a | b | ΔE color build-up |
| --- | --- | --- | --- | --- |
| 0 shampoo washes | 40.87 | 19.96 | 18.72 | 29.18 |
| 5 shampoo washes | 48.58 | 15.5 | 18.85 | 20.44 |

Visually, the intense red coloring appears unchanged between the coloring obtained just after having performed the process of the invention and after 1 and 5 successive shampoo washes. In addition, the hair strands appear individualized after treatment, with a respected volume, and this is found even after 5 shampoo washes. The feel is very pleasant.

The invention claimed is:
1. A process for treating keratin fibers, comprising:
1a) applying to the keratin fibers an oily dispersion (A), wherein the oily dispersion (A) comprises:
  i) at least one particle comprising at least one ethylenic copolymer of:
    a) $C_1$-$C_4$)alkyl ($C_1$-$C_4$)(alkyl)acrylate, and
    b) ethylenically unsaturated anhydride compound;
  ii) at least one stabilizer comprising at least one ethylenic polymer chosen from:
    c) polymers of ($C_3$-$C_{12}$)cycloalkyl ($C_1$-$C_6$)(alkyl) acrylate monomers,
    d) copolymers of ($C_3$-$C_{12}$)cycloalkyl ($C_1$-$C_6$)(alkyl)acrylate and ($C_1$-$C_4$)alkyl ($C_1$-$C_4$)(alkyl) acrylate, or
    a combination thereof; and
  iii) at least one hydrocarbon-based oil; and
1b) subsequently applying to the keratin fibers a composition (B), wherein the composition (B) comprises:
  iv) at least one amine compound chosen from:
    e) polyamine compounds bearing several primary amine and/or secondary amine groups,
    f) amino alkoxysilanes, or
    a combination thereof; or
2) applying to the keratin fibers an oily dispersion (D), wherein the oily dispersion (D) comprises:
  i) at least one particle comprising at least one ethylenic copolymer of:
    a) $C_1$-$C_4$)alkyl ($C_1$-$C_4$)(alkyl)acrylate, and
    b) ethylenically unsaturated anhydride compound;
  ii) at least one stabilizer comprising at least one ethylenic polymer chosen from:
    c) polymers of ($C_3$-$C_{12}$)cycloalkyl ($C_1$-$C_6$)(alkyl) acrylate monomers,
    d) copolymers of ($C_3$-$C_{12}$)cycloalkyl ($C_1$-$C_6$)(alkyl)acrylate and ($C_1$-$C_4$)alkyl ($C_1$-$C_4$)(alkyl) acrylate, or
    a combination thereof;
  iii) at least one hydrocarbon-based oil; and
  iv) at least one amine compound chosen from:
    e) polyamine compounds bearing several primary amine and/or secondary amine groups,
    f) amino alkoxysilanes, or
    a combination thereof; and
3) optionally, applying to the keratin fibers a composition (C) comprising v) at least one dye and/or at least one pigment;
wherein dispersion (A), dispersion (D), and/or composition (B) optionally further comprises v) at least one dye and/or pigment.

2. The process of claim 1, wherein the a) ($C_1$-$C_4$)alkyl ($C_1$-$C_4$)(alkyl)acrylate is chosen from those of formula:

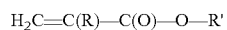

wherein R is chosen from a hydrogen atom or a ($C_1$-$C_4$) alkyl group, and R' is chosen from a ($C_1$-$C_4$)alkyl group.

3. The process of claim 1, wherein the b) ethylenically unsaturated anhydride compound is chosen from derivatives of the maleic anhydride of formula (Ib) and the itaconic anhydride of formula (IIb):

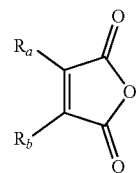

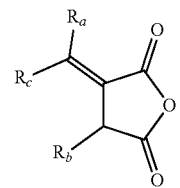

wherein in formulae (Ib) and (IIb), $R_a$, $R_b$ and $R_c$, which may be identical or different, are chosen from a hydrogen atom or a ($C_1$-$C_4$)alkyl group.

4. The process of claim 1, wherein the i) at least one particle of the dispersion (A) or (D) comprises from 80% to 99.99% by weight of the a) $C_1$-$C_4$)alkyl ($C_1$-$C_4$)(alkyl) acrylate, and from 0.01% to 20% by weight of the b) ethylenically unsaturated anhydride compound, relative to the total weight of the at least one particle.

5. The process of claim 1, wherein the at least one particle i) is present in dispersion (A) or (D) in an amount ranging from 20% to 60% by weight, relative to the total weight of the dispersion (A) or (D).

6. The process of claim 1, wherein the ii) at least one stabilizer of dispersion (A) or (D) comprises at least one ethylenic polymer chosen from:

c) polymers of monomers of formula H₂C=C(R)—C(O)—O—R", wherein R is chosen from a hydrogen atom or a (C₁-C₄)alkyl group, and R" is chosen from a (C₅-C₁₀)cycloalkyl group;

d) copolymers of H₂C=C(R)—C(O)—O—R' and H₂C=C(R)—C(O)—O—R", wherein R is chosen from a hydrogen atom or a (C₁-C₄)alkyl group, R' is chosen from a (C₁-C₄)alkyl group, and R" is chosen from a (C₅-C₁₀)cycloalkyl group; or mixtures thereof.

7. The process of claim 1, wherein the dispersion (A) or (D) comprises from 10% to 50% by weight of at least one ethylenic polymer chosen from copolymers d), and from 50 to 90% by weight of at least one ethylenic polymer chosen from polymers c), relative to the total weight of the sum of the i) at least one particle and the ii) at least one stabilizer.

8. The process of claim 1, wherein the iii) at least one hydrocarbon-based oil is chosen from volatile apolar oils, and consists of carbon and hydrogen atoms.

9. The process of claim 1, wherein the dispersion (A) or (D) is in inverse emulsion of water-in-oil (W/O) type, and further comprises at least one surfactant.

10. The process of claim 1, wherein the at least one amine compound of composition (B) or of dispersion (D) is chosen from the amino alkoxysilanes f) of formula (IVa):

(IVa)

wherein in formula (IVa):
R'₁ is a linear or branched, saturated or unsaturated, cyclic or acyclic C₁-C₁₀ hydrocarbon-based chain substituted with a group chosen from:
primary amine NH₂ or secondary amine N(H)R, wherein R is chosen from a (C₁-C₄)alkyl group, and
an aryl or aryloxy group substituted with an amino or (C₁-C₄)alkylamino group or with a C₁-C₄ aminoalkyl group; or
wherein R'₁ is optionally interrupted in its chain with a heteroatom or a carbonyl group (CO), and R'₁ being linked to a silicon atom directly via a carbon atom;
R'₂ and R'₃, which may be identical or different, represent a linear or branched alkyl group comprising from 1 to 6 carbon atoms;
z denotes an integer ranging from 1 to 3; and
x denotes an integer ranging from 0 to 2;
wherein z+x=3.

11. The process of claim 10, wherein the amino alkoxysilanes of formula (IVa) are chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane, or N-(2-aminoethylaminomethyl)phenethyltrimethoxysilane.

12. The process of claim 1, wherein the at least one amine compound of composition (B) or of dispersion (D) chosen from the e) polyamine compounds bearing several primary amine and/or secondary amine groups is chosen from:
poly((C₂-C₅)alkyleneimines);
poly(allylamines);
polyvinylamines and copolymers thereof;
polyamino acids containing NH₂ groups;
aminodextran;
amino polyvinyl alcohol;
copolymers based on acrylamidopropylamine;
chitosans;
polydi(C₁-C₄)alkylsiloxanes comprising amine groups at the chain end or on side chains; or
mixtures thereof.

13. The process of claim 12, wherein the polydi(C₁-C₄)alkylsiloxanes comprising amine groups at the chain end or on side chains are chosen from:
polyamine compounds comprising end or side amino(C₁-C₆)alkyl groups of formula (IVb), (IVc), or (IVd):

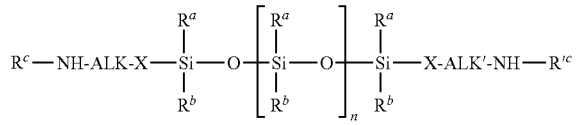

(IVb)

wherein in formula (IVb):
R$^a$ and R$^b$, which may be identical or different, are chosen from a (C₁-C₄)alkyl group, (C₁-C₄)alkoxy, aryl, aryloxy, aryl(C₁-C₄)alkyl, or an aryl(C₁-C₄)alkoxy;
R$^c$ and R$^{lc}$, which may be identical or different, are chosen from a hydrogen atom, a (C₁-C₄)alkyl group, an amino(C₁-C₄)alkyl, or (C₁-C₄)alkylamino(C₁-C₄)alkyl group;
X represents a covalent bond or an oxygen atom;
ALK and ALK', which may be identical or different, represent a (C₁-C₆)alkylene group; and
n represents an integer greater than 2;

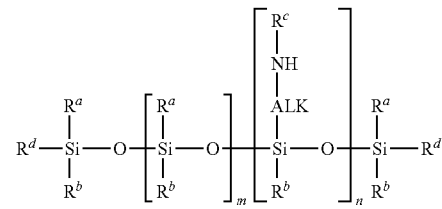

(IVc)

wherein in formula (IVc):
R$^a$, R$^b$, and R$^d$, which may be identical or different, are chosen from a (C₁-C₄)alkyl group, (C₁-C₄)alkoxy, aryl, aryloxy, aryl(C₁-C₄)alkyl, or aryl(C₁-C₄)alkoxy, wherein R$^d$ may also represent a (C₁-C₆)alkyl group substituted with a (C₁-C₄)alkylamino or an amino group;
R$^c$ is chosen from a hydrogen atom or a (C₁-C₄)alkyl group;
ALK represents a (C₁-C₆)alkyl group; and
n and m, which may be identical or different, represent an integer greater than 2;

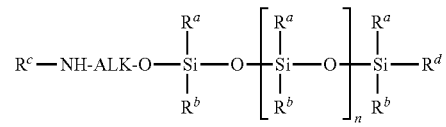

(IVd)

wherein in formula (IVd):
R$^a$ and R$^b$, which may be identical or different, are chosen from a (C₁-C₄)alkyl groups, (C₁-C₄)alkoxy, aryl, aryloxy, aryl(C₁-C₄)alkyl, or aryl(C₁-C₄)alkoxy;

$R^d$ is chosen from a $(C_1-C_6)$alkyl group optionally substituted with a $(C_1-C_4)$alkylamino or amino group;

$R^c$ is chosen from a hydrogen atom or a $(C_1-C_4)$alkyl group;

ALK represents a $(C_1-C_6)$alkylene group; and n represents an integer greater than 2; and amodimethicones of formula (IVe):

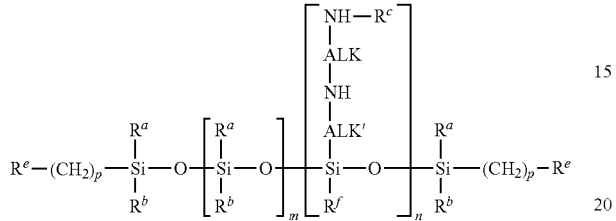

(IVe)

wherein in formula (IVe)

$R^a$ and $R^b$, which may be identical or different, are chosen from a $(C_1-C_4)$alkyl group, $(C_1-C_4)$alkoxy, aryl, aryloxy, aryl$(C_1-C_4)$alkyl, or aryl$(C_1-C_4)$alkoxy;

$R^c$ is chosen from a hydrogen atom or a $(C_1-C_4)$alkyl group;

$R^e$ is chosen from a hydroxyl, $(C_1-C_4)$alkoxy, amino or $(C_1-C_4)$alkylamino group;

$R^f$ is chosen from a $(C_1-C_4)$alkyl group, a $(C_1-C_4)$alkoxy group, a hydroxyl or —O—$(SiR_2)_x$—R' group, wherein R represents a $(C_1-C_4)$alkyl or $(C_1-C_4)$alkoxy group and R' represents a $(C_1-C_4)$alkoxy or hydroxyl group;

$R^g$ is chosen from a hydrogen atom or a $(C_1-C_6)$alkyl group;

ALK and ALK', which may be identical or different, represent a $(C_1-C_6)$alkylene group;

n and m, which may be identical or different, represent an integer greater than 2, and p and x are integers greater than or equal to 0.

14. The process of claim 13, wherein:

the polydi$(C_1-C_4)$alkylsiloxanes of formula (IVb) are chosen from compounds of formula (IV'b) and (IV''b) below:

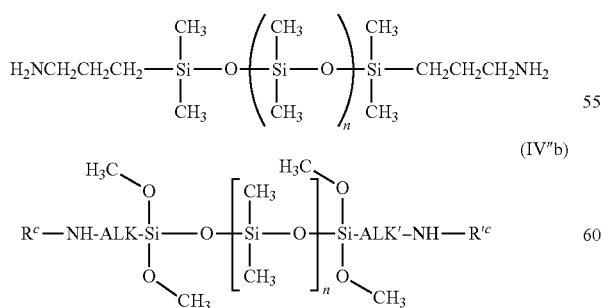

wherein in formula (IV'b), the value of n is such that the weight-average molecular weight of the compound is between 500 and 55 000; and wherein in formula (IV''b), $R^c$, $R'^c$, ALK, ALK, and n are as defined previously for those in formula (IVb);

the polydi$(C_1-C_4)$alkylsiloxanes of formula (IVc) are chosen from compounds of the following formula (IV'c)

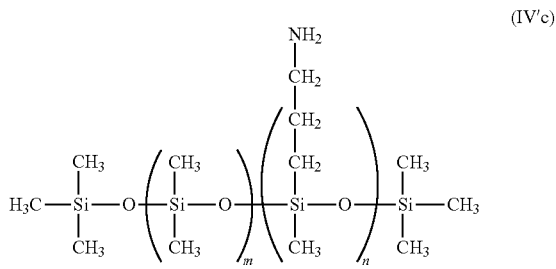

(IV'c)

wherein in formula (IV'c), the values of n and m are such that the weight-average molecular weight of the compound is between 1000 and 55 000;

the polydi$(C_1-C_4)$alkylsiloxanes of formula (IVd) are chosen from compounds of the following formula (IV'd):

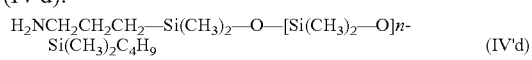

$H_2NCH_2CH_2CH_2$—$Si(CH_3)_2$—O—$[Si(CH_3)_2$—O$]n$-$Si(CH_3)_2C_4H_9$ (IV'd)

wherein in formula (Iv'd), the value of n is such that the weight-average molecular weight of the compound is between 500 and 3000;

the amodimethicones of formula (IVe) are chosen from compounds of formula (IV'e) and formula (IV''e) below:

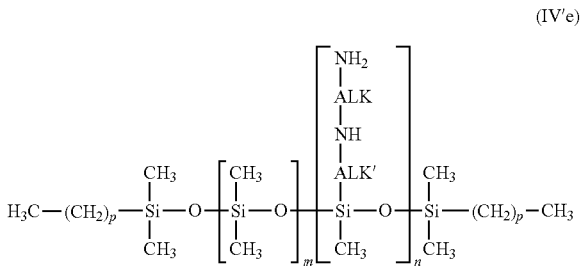

(IV'e)

wherein in formula (IV'e):

ALK represents a $(C_1-C_6)$alkylene group;

ALK' represents a $(C_1-C_6)$alkylene group; and m, n and p, which may be identical or different, represent an integer greater than 2, wherein the values of m, n and p are such that the weight-average molecular weight of the compound is between approximately 5000 and 500 000;

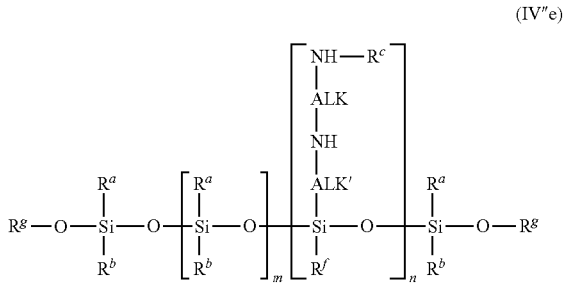

(IV''e)

wherein in formula (IV"e):
R$^a$ and R$^b$, which may be identical or different, are chosen from a (C$_1$-C$_4$)alkyl group or a (C$_1$-C$_4$) alkoxy group;
R$^c$ is chosen from a hydrogen atom or a (C$_1$-C$_4$)alkyl group;
R$^f$ is chosen from a (C$_1$-C$_4$)alkyl group, a (C$_1$-C$_4$) alkoxy group, or —O—(SiR$_2$)$_x$—R', wherein R represents a (C$_1$-C$_4$)alkyl group and R' represents a hydroxyl or (C$_1$-C$_4$)alkoxy group;
R$^g$ is chosen from a hydrogen atom or a (C$_1$-C$_6$)alkyl group;
ALK represents a (C$_1$-C$_6$)alkylene group;
ALK' represents a (C$_1$-C$_6$)alkylene group;
n and m, which may be identical or different, represent an integer greater than 2; and
x is an integer greater than or equal to 0;
wherein the values of m, n and x are such that the weight-average molecular weight of the compound is between 2000 and 700,000.

15. The process of claim 1, wherein composition (B) further comprises the iii) at least one hydrocarbon-based oil.

16. The process of claim 1, wherein composition (B) is aqueous and further comprises at least one chitosan and/or at least one polyamino acid.

17. The process of claim 1, wherein composition (B) is anhydrous.

18. The process of claim 1, wherein:
the at least one dye is chosen from:
oxidation dyes including at least one oxidation bases, optionally combined with one or more coupling agents;
direct dyes chosen from azo direct dyes, (poly)methine dyes, carbonyl dyes, azine dyes, nitro(hetero)aryl dyes, tri(hetero)arylmethane dyes, porphyrin dyes, phthalocyanine dyes, natural direct dyes;
natural dyes chosen from hennotannic acid, juglone, alizarin, purpurin, carminic acid, kermesic acid, purpurogallin, protocatechaldehyde, indigo, isatin, curcumin, spinulosin, apigenidin, orcein, or extracts or decoctions containing these natural dyes; or
a combination thereof; and
the at least one pigment is chosen from:
organic nitroso pigment, nitro pigment, azo pigment, xanthene pigment, quinoline pigment, anthraquinone pigment, phthalocyanin pigment, metal complex type pigment, isoindolinone, isoindoline, quinacridone, perinone, perylene, diketopyrrolopyrrole, thioindigo, dioxazine, triphenylmethane, or quinophthalone;
mineral or inorganic pigments chosen from iron or chromium oxides, manganese violet, ultramarine blue, chromium hydrate, ferric blue, or titanium oxide, or
a combination thereof.

19. The process of claim 1,
wherein the at least one pigment is chosen from organic pigments, mineral or inorganic pigments, fluorescent pigments, thermochromic pigments, photochromic pigments, coated or uncoated nacres in the form of pigment powder or paste, lakes, glitter flakes, or mixtures thereof;
wherein the at least one pigment is dispersed in the disperse (A), composition (B), and/or disperse (D); and
wherein the at least one pigment is surface-treated with an organic agent.

20. The process of claim 1, wherein composition (C) is applied to the keratin fibers after the oily dispersion (A) is applied to the keratin fibers and before composition (B) is applied to the keratin fibers.

21. The process of claim 1, wherein the oily dispersion (A) is applied to the keratin fibers after composition (C) is applied to the keratin fibers and before composition (B) is applied to the keratin fibers.

22. The process of claim 1, wherein after applying to the keratin fibers the oily dispersion (A) and before applying to the keratin fibers composition (B), without rinsing, the keratin fibers are dried in the air or by using a drying device.

23. The process of claim 1, wherein composition (C) is applied to the keratin fibers before the oily dispersion (D) is applied to the keratin fibers.

24. A kit comprising:
a first compartment comprising a dispersion (A), wherein the dispersion (A) comprises:
i) at least one particle comprising at least one ethylenic copolymer of:
a) C$_1$-C$_4$)alkyl (C$_1$-C$_4$)(alkyl)acrylate, and
b) ethylenically unsaturated anhydride compound;
ii) at least one stabilizer comprising at least one ethylenic polymer chosen from:
c) polymers of (C$_3$-C$_{12}$)cycloalkyl (C$_1$-C$_6$)(alkyl)acrylate monomers,
d) copolymers of (C$_3$-C$_{12}$)cycloalkyl (C$_1$-C$_6$)(alkyl) acrylate and (C$_1$-C$_4$)alkyl (C$_1$-C$_4$)(alkyl)acrylate, or
a combination thereof; and
iii) at least one hydrocarbon-based oil;
a second compartment comprising a composition (B), wherein the composition (B) comprises:
iv) at least one amine compound chosen from:
e) polyamine compounds bearing several primary amine and/or secondary amine groups,
f) amino alkoxysilanes, or
a combination thereof; and
optionally a third compartment comprising a composition (C), wherein the composition (C) comprises at least one dye and/or at least one pigment.

25. An oily dispersion (A) comprising:
i) at least one particle comprising at least one ethylenic copolymer of:
a) C$_1$-C$_4$)alkyl (C$_1$-C$_4$)(alkyl)acrylate, and
b) ethylenically unsaturated anhydride compound;
ii) at least one stabilizer comprising at least one ethylenic polymer chosen from:
c) polymers of (C$_3$-C$_{12}$)cycloalkyl (C$_1$-C$_6$)(alkyl)acrylate monomers,
d) copolymers of (C$_3$-C$_{12}$)cycloalkyl (C$_1$-C$_6$)(alkyl) acrylate and (C$_1$-C$_4$)alkyl (C$_1$-C$_4$)(alkyl)acrylate, or
a combination thereof;
iii) at least one hydrocarbon-based oil; and
v) optionally at least one dye and/or at least one pigment,
wherein when the at least one pigment is present, the oily dispersion (A) is anhydrous and does not comprise any polyamine compound bearing primary amine and/or secondary amine groups, and does not comprise any amino alkoxysilanes.

26. The oily dispersion (A) of claim 25, wherein the oily dispersion (A) is in emulsion of water-in-oil (W/O) type, and further comprises at least one surfactant.

* * * * *